US011583489B2

(12) United States Patent
Miller, IV et al.

(10) Patent No.: US 11,583,489 B2
(45) Date of Patent: Feb. 21, 2023

(54) FLUSHABLE WIPE AND METHOD OF FORMING THE SAME

(71) Applicant: First Quality Tissue, LLC, Great Neck, NY (US)

(72) Inventors: Byrd Tyler Miller, IV, Easley, SC (US); James E. Sealey, II, Belton, SC (US); Justin S. Pence, Anderson, SC (US); Taras Z. Andrukh, Greenville, SC (US); Zachary Korkowski, Greenville, SC (US); Ashley Harris, Inman, SC (US)

(73) Assignee: FIRST QUALITY TISSUE, LLC, Great Neck, NY (US)

( * ) Notice: Subject to any disclaimer, the term of this patent is extended or adjusted under 35 U.S.C. 154(b) by 0 days.

(21) Appl. No.: 15/355,358

(22) Filed: Nov. 18, 2016

(65) Prior Publication Data
US 2018/0140529 A1 May 24, 2018

(51) Int. Cl.
| | |
|---|---|
| A61K 8/73 | (2006.01) |
| D21H 17/66 | (2006.01) |
| D21H 17/65 | (2006.01) |
| A61K 8/81 | (2006.01) |
| B33Y 80/00 | (2015.01) |
| A61K 8/02 | (2006.01) |
| A61K 8/19 | (2006.01) |
| A61K 8/60 | (2006.01) |
| A61K 8/66 | (2006.01) |
| A61K 8/88 | (2006.01) |
| A61K 8/92 | (2006.01) |
| A61K 8/97 | (2017.01) |
| A61Q 19/00 | (2006.01) |
| A61Q 19/10 | (2006.01) |
| D21H 17/36 | (2006.01) |
| D21H 27/00 | (2006.01) |
| D21H 27/32 | (2006.01) |
| D21H 27/40 | (2006.01) |
| B33Y 10/00 | (2015.01) |

(52) U.S. Cl.
CPC ............ *A61K 8/731* (2013.01); *A61K 8/0208* (2013.01); *A61K 8/19* (2013.01); *A61K 8/602* (2013.01); *A61K 8/66* (2013.01); *A61K 8/8129* (2013.01); *A61K 8/8135* (2013.01); *A61K 8/8158* (2013.01); *A61K 8/88* (2013.01); *A61K 8/922* (2013.01); *A61K 8/97* (2013.01); *A61Q 19/00* (2013.01); *A61Q 19/10* (2013.01); *B33Y 80/00* (2014.12); *D21H 17/36* (2013.01); *D21H 17/65* (2013.01); *D21H 17/66* (2013.01); *D21H 27/007* (2013.01); *D21H 27/32* (2013.01); *D21H 27/40* (2013.01); *A61K 2800/805* (2013.01); *B33Y 10/00* (2014.12)

(58) Field of Classification Search
CPC ........ A61K 8/731; A61K 8/0208; A61K 8/19; A61K 8/602; A61K 8/66; A61K 8/8129; B33Y 80/00
See application file for complete search history.

(56) References Cited

U.S. PATENT DOCUMENTS

| | | | |
|---|---|---|---|
| 2,919,467 | A | 1/1960 | Mercer |
| 2,926,154 | A | 2/1960 | Keim |
| 3,026,231 | A | 3/1962 | Chavannes |
| 3,049,469 | A | 8/1962 | Davison |
| 3,058,873 | A | 10/1962 | Keim et al. |
| 3,066,066 | A | 11/1962 | Keim et al. |
| 3,097,994 | A | 7/1963 | Dickens et al. |
| 3,125,552 | A | 3/1964 | Loshaek et al. |
| 3,143,150 | A | 8/1964 | Buchanan |
| 3,186,900 | A | 6/1965 | De Young |
| 3,197,427 | A | 7/1965 | Schmalz |
| 3,224,986 | A | 12/1965 | Butler et al. |
| 3,224,990 | A | 12/1965 | Babcock |
| 3,227,615 | A | 1/1966 | Korden |
| 3,227,671 | A | 1/1966 | Keim |
| 3,239,491 | A | 3/1966 | Tsou et al. |
| 3,240,664 | A | 3/1966 | Earle, Jr. |
| 3,240,761 | A | 3/1966 | Keim et al. |
| 3,248,280 | A | 4/1966 | Hyland, Jr. |
| 3,250,664 | A | 5/1966 | Conte et al. |
| 3,252,181 | A | 5/1966 | Hureau |

(Continued)

FOREIGN PATENT DOCUMENTS

| | | |
|---|---|---|
| CA | 2168894 A1 | 8/1997 |
| CA | 2795139 A1 | 10/2011 |
| CN | 1138356 A | 12/1996 |
| CN | 1207149 A | 2/1999 |
| CN | 1244899 A | 2/2000 |

(Continued)

OTHER PUBLICATIONS

International Preliminary Report on Patentability of PCT/US2013/053593 dated Feb. 3, 2015.
Supplementary European Search Report of EP 13 82 6461 dated Apr. 1, 2016.
International Search Report of PCT/US17/60608 dated Jan. 5, 2018.

(Continued)

*Primary Examiner* — Genevieve S Alley
(74) *Attorney, Agent, or Firm* — Amster, Rothstein & Ebenstein LLP

(57) ABSTRACT

A single or multi-ply flushable and dispersible wet wipe including a wet laid fibrous web imprinted using a structuring fabric, a binder composition comprising poly(vinyl) alcohol, poly(vinyl) acetate, poly (ethylene) (vinyl) alcohols, poly (ethylene) (vinyl) acetate, copolymers of vinyl acetate-ethylene, or combinations thereof, and one or more additives. In an exemplary embodiment, the fibrous web is wetted by a wetting solution comprising 0.1% to about 10% by weight of one of the following: (1) boric acid; and (2) boric acid and a mono or divalent salt.

1 Claim, 4 Drawing Sheets

(56) References Cited

U.S. PATENT DOCUMENTS

| | | |
|---|---|---|
| 3,301,746 A | 1/1967 | Sanford et al. |
| 3,311,594 A | 3/1967 | Earle, Jr. |
| 3,329,657 A | 7/1967 | Strazdins et al. |
| 3,332,834 A | 7/1967 | Reynolds, Jr. |
| 3,332,901 A | 7/1967 | Keim |
| 3,352,833 A | 11/1967 | Earle, Jr. |
| 3,384,692 A | 5/1968 | Galt et al. |
| 3,414,459 A | 12/1968 | Wells |
| 3,442,754 A | 5/1969 | Espy |
| 3,459,697 A | 8/1969 | Goldberg et al. |
| 3,473,576 A | 10/1969 | Amneus |
| 3,483,077 A | 12/1969 | Aldrich |
| 3,545,165 A | 12/1970 | Greenwell |
| 3,556,932 A | 1/1971 | Coscia et al. |
| 3,573,164 A | 3/1971 | Friedberg et al. |
| 3,609,126 A | 9/1971 | Asao et al. |
| 3,666,609 A | 5/1972 | Kalwaites et al. |
| 3,672,949 A | 6/1972 | Brown |
| 3,672,950 A | 6/1972 | Murphy et al. |
| 3,773,290 A | 11/1973 | Mowery |
| 3,778,339 A | 12/1973 | Williams et al. |
| 3,813,362 A | 5/1974 | Coscia et al. |
| 3,855,158 A | 12/1974 | Petrovich et al. |
| 3,877,510 A | 4/1975 | Tegtmeier et al. |
| 3,905,863 A | 9/1975 | Ayers |
| 3,911,173 A | 10/1975 | Sprague, Jr. |
| 3,974,025 A | 8/1976 | Ayers |
| 3,994,771 A | 11/1976 | Morgan, Jr. et al. |
| 3,998,690 A | 12/1976 | Lyness et al. |
| 4,038,008 A | 7/1977 | Larsen |
| 4,075,382 A | 2/1978 | Chapman et al. |
| 4,088,528 A | 5/1978 | Berger et al. |
| 4,098,632 A | 7/1978 | Sprague, Jr. |
| 4,102,737 A | 7/1978 | Morton |
| 4,117,187 A | 9/1978 | Adams et al. |
| 4,129,528 A | 12/1978 | Petrovich et al. |
| 4,147,586 A | 4/1979 | Petrovich et al. |
| 4,184,519 A | 1/1980 | McDonald et al. |
| 4,190,692 A | 2/1980 | Larsen |
| 4,191,609 A | 3/1980 | Trokhan |
| 4,252,761 A | 2/1981 | Schoggen et al. |
| 4,258,849 A | 3/1981 | Miller |
| 4,309,469 A | 1/1982 | Varona |
| 4,320,162 A | 3/1982 | Schulz |
| 4,331,510 A | 5/1982 | Wells |
| 4,382,987 A | 5/1983 | Smart |
| 4,440,597 A | 4/1984 | Wells et al. |
| 4,501,862 A | 2/1985 | Keim |
| 4,507,351 A | 3/1985 | Johnson et al. |
| 4,514,345 A | 4/1985 | Johnson et al. |
| 4,515,657 A | 5/1985 | Maslanka |
| 4,528,239 A | 7/1985 | Trokhan |
| 4,529,480 A | 7/1985 | Trokhan |
| 4,537,657 A | 8/1985 | Keim |
| 4,545,857 A | 10/1985 | Wells |
| 4,637,859 A | 1/1987 | Trokhan |
| 4,678,590 A | 7/1987 | Nakamura et al. |
| 4,714,736 A | 12/1987 | Juhl et al. |
| 4,770,920 A | 9/1988 | Larsonneur |
| 4,780,357 A | 10/1988 | Akao |
| 4,808,467 A | 2/1989 | Suskind et al. |
| 4,836,894 A | 6/1989 | Chance et al. |
| 4,849,054 A | 7/1989 | Klowak |
| 4,885,202 A | 12/1989 | Lloyd et al. |
| 4,891,249 A | 1/1990 | McIntyre |
| 4,909,284 A | 3/1990 | Kositake |
| 4,949,668 A | 8/1990 | Heindel et al. |
| 4,949,688 A | 8/1990 | Bayless |
| 4,983,256 A | 1/1991 | Combette et al. |
| 4,996,091 A | 2/1991 | McIntyre |
| 5,059,282 A | 10/1991 | Ampulski et al. |
| 5,143,776 A | 9/1992 | Givens |
| 5,149,401 A | 9/1992 | Langevin et al. |
| 5,152,874 A | 10/1992 | Keller |
| 5,211,813 A | 5/1993 | Sawley et al. |
| 5,239,047 A | 8/1993 | Devore et al. |
| 5,279,098 A | 1/1994 | Fukuda |
| 5,281,306 A | 1/1994 | Kakiuchi et al. |
| 5,334,289 A | 8/1994 | Trokhan et al. |
| 5,347,795 A | 9/1994 | Fukuda |
| 5,397,435 A | 3/1995 | Ostendorf et al. |
| 5,399,412 A | 3/1995 | Sudall et al. |
| 5,405,501 A | 4/1995 | Phan et al. |
| 5,409,572 A | 4/1995 | Kershaw et al. |
| 5,429,686 A | 7/1995 | Chiu et al. |
| 5,439,559 A | 8/1995 | Crouse |
| 5,447,012 A | 9/1995 | Kovacs et al. |
| 5,470,436 A | 11/1995 | Wagle et al. |
| 5,487,313 A | 1/1996 | Johnson |
| 5,509,913 A | 4/1996 | Yeo |
| 5,510,002 A | 4/1996 | Hermans et al. |
| 5,529,665 A | 6/1996 | Kaun |
| 5,581,906 A | 12/1996 | Ensign et al. |
| 5,591,147 A | 1/1997 | Couture-Dorschner et al. |
| 5,607,551 A | 3/1997 | Farrington, Jr. et al. |
| 5,611,890 A | 3/1997 | Vinson et al. |
| 5,628,876 A | 5/1997 | Ayers et al. |
| 5,629,081 A | 5/1997 | Richards et al. |
| 5,635,028 A | 6/1997 | Vinson et al. |
| 5,649,916 A | 7/1997 | Dipalma et al. |
| 5,671,897 A | 9/1997 | Ogg et al. |
| 5,672,248 A | 9/1997 | Wendt et al. |
| 5,679,222 A | 10/1997 | Rasch et al. |
| 5,685,428 A | 11/1997 | Herbers et al. |
| 5,728,268 A | 3/1998 | Weisman et al. |
| 5,746,887 A | 5/1998 | Wendt et al. |
| 5,753,067 A | 5/1998 | Fukuda et al. |
| 5,772,845 A | 6/1998 | Farrington, Jr. et al. |
| 5,806,569 A | 9/1998 | Gulya et al. |
| 5,827,384 A | 10/1998 | Canfield et al. |
| 5,832,962 A | 11/1998 | Kaufman et al. |
| 5,846,380 A | 12/1998 | Van Phan et al. |
| 5,855,738 A | 1/1999 | Weisman et al. |
| 5,858,554 A | 1/1999 | Neal et al. |
| 5,865,396 A | 2/1999 | Ogg et al. |
| 5,865,950 A | 2/1999 | Vinson et al. |
| 5,893,965 A | 4/1999 | Trokhan et al. |
| 5,913,765 A | 6/1999 | Burgess et al. |
| 5,942,085 A | 8/1999 | Neal et al. |
| 5,944,954 A | 8/1999 | Vinson et al. |
| 5,948,210 A | 9/1999 | Huston |
| 5,980,691 A | 11/1999 | Weisman et al. |
| 6,036,139 A | 3/2000 | Ogg |
| 6,039,838 A | 3/2000 | Kaufman et al. |
| 6,048,938 A | 4/2000 | Neal et al. |
| 6,060,149 A | 5/2000 | Nissing et al. |
| 6,106,670 A | 8/2000 | Weisman et al. |
| 6,149,769 A | 11/2000 | Mohammadi et al. |
| 6,162,327 A | 12/2000 | Batra et al. |
| 6,162,329 A | 12/2000 | Vinson et al. |
| 6,187,138 B1 | 2/2001 | Neal et al. |
| 6,200,419 B1 | 3/2001 | Phan |
| 6,203,667 B1 | 3/2001 | Huhtelin |
| 6,207,734 B1 | 3/2001 | Vinson et al. |
| 6,231,723 B1 | 5/2001 | Kanitz et al. |
| 6,287,426 B1 | 9/2001 | Edwards et al. |
| 6,303,233 B1 | 10/2001 | Amon et al. |
| 6,319,362 B1 | 11/2001 | Huhtelin et al. |
| 6,344,111 B1 | 2/2002 | Wilhelm |
| 6,420,013 B1 | 7/2002 | Vinson et al. |
| 6,420,100 B1 | 7/2002 | Trokhan et al. |
| 6,423,184 B2 | 7/2002 | Vahatalo et al. |
| 6,458,246 B1 | 10/2002 | Kanitz et al. |
| 6,464,831 B1 | 10/2002 | Trokhan et al. |
| 6,473,670 B1 | 10/2002 | Huhtelin |
| 6,521,089 B1 | 2/2003 | Griech et al. |
| 6,537,407 B1 | 3/2003 | Law et al. |
| 6,547,928 B2 | 4/2003 | Barnholtz et al. |
| 6,551,453 B2 | 4/2003 | Weisman et al. |
| 6,551,691 B1 | 4/2003 | Hoeft et al. |
| 6,572,722 B1 | 6/2003 | Pratt |
| 6,574,211 B2 | 6/2003 | Morita |
| 6,579,416 B1 | 6/2003 | Vinson et al. |
| 6,602,454 B2 | 8/2003 | McGuire et al. |

(56) References Cited

U.S. PATENT DOCUMENTS

| | | |
|---|---|---|
| 6,607,637 B1 | 8/2003 | Vinson et al. |
| 6,610,173 B1 | 8/2003 | Lindsay et al. |
| 6,613,194 B2 | 9/2003 | Kanitz et al. |
| 6,660,362 B1 | 12/2003 | Lindsay et al. |
| 6,673,202 B2 | 1/2004 | Burazin |
| 6,728,277 B1 | 4/2004 | Wilson et al. |
| 6,701,637 B2 | 5/2004 | Lindsay et al. |
| 6,755,939 B2 | 6/2004 | Vinson et al. |
| 6,773,647 B2 | 8/2004 | McGuire et al. |
| 6,797,117 B1 | 9/2004 | McKay et al. |
| 6,808,599 B2 | 10/2004 | Burazin |
| 6,821,386 B2 | 11/2004 | Weisman et al. |
| 6,821,391 B2 | 11/2004 | Scherb et al. |
| 6,823,568 B1 | 11/2004 | Kobayashi. et al. |
| 6,827,818 B2 | 12/2004 | Farrington, Jr. et al. |
| 6,863,777 B2 | 3/2005 | Kanitz et al. |
| 6,896,767 B2 | 5/2005 | Wilhelm |
| 6,939,443 B2 | 9/2005 | Ryan et al. |
| 6,998,017 B2 | 2/2006 | Lindsay et al. |
| 6,998,024 B2 | 2/2006 | Burazin |
| 7,005,043 B2 | 2/2006 | Toney et al. |
| 7,014,735 B2 | 3/2006 | Kramer et al. |
| 7,105,465 B2 | 9/2006 | Patel et al. |
| 7,155,876 B2 | 1/2007 | VanderTuin et al. |
| 7,157,389 B2 | 1/2007 | Branham et al. |
| 7,182,837 B2 | 2/2007 | Chen et al. |
| 7,194,788 B2 | 3/2007 | Clark et al. |
| 7,235,156 B2 | 6/2007 | Baggot |
| 7,269,929 B2 | 9/2007 | VanderTuin et al. |
| 7,294,230 B2 | 11/2007 | Flugge-Berendes et al. |
| 7,311,853 B2 | 12/2007 | Vinson et al. |
| 7,328,550 B2 | 2/2008 | Floding et al. |
| 7,339,378 B2 | 3/2008 | Han et al. |
| 7,351,307 B2 | 4/2008 | Scherb et al. |
| 7,387,706 B2 | 6/2008 | Herman et al. |
| 7,399,378 B2 | 7/2008 | Edwards et al. |
| 7,419,569 B2 | 9/2008 | Hermans |
| 7,427,434 B2 | 9/2008 | Busam |
| 7,431,801 B2 | 10/2008 | Conn et al. |
| 7,432,309 B2 | 10/2008 | Vinson |
| 7,442,278 B2 | 10/2008 | Murray et al. |
| 7,452,447 B2 | 11/2008 | Duan et al. |
| 7,476,293 B2 | 1/2009 | Herman et al. |
| 7,494,563 B2 | 2/2009 | Edwards et al. |
| 7,510,631 B2 | 3/2009 | Scherb et al. |
| 7,513,975 B2 | 4/2009 | Burma |
| 7,563,344 B2 | 7/2009 | Beuther |
| 7,582,187 B2 | 9/2009 | Scherb et al. |
| 7,611,607 B2 | 11/2009 | Mullally et al. |
| 7,622,020 B2 | 11/2009 | Awofeso |
| 7,662,462 B2 | 2/2010 | Noda |
| 7,670,678 B2 | 3/2010 | Phan |
| 7,683,126 B2 | 3/2010 | Neal et al. |
| 7,686,923 B2 | 3/2010 | Scherb et al. |
| 7,687,140 B2 | 3/2010 | Manifold et al. |
| 7,691,230 B2 | 4/2010 | Scherb et al. |
| 7,744,722 B1 | 6/2010 | Tucker et al. |
| 7,744,726 B2 | 6/2010 | Scherb et al. |
| 7,799,382 B2 | 9/2010 | Payne et al. |
| 7,811,418 B2 | 10/2010 | Klerelid et al. |
| 7,815,978 B2 | 10/2010 | Davenport et al. |
| 7,823,366 B2 | 11/2010 | Schoeneck |
| 7,842,163 B2 | 11/2010 | Nickel et al. |
| 7,867,361 B2 | 1/2011 | Salaam et al. |
| 7,871,692 B2 | 1/2011 | Morin et al. |
| 7,879,191 B2 | 2/2011 | Dyer et al. |
| 7,887,673 B2 | 2/2011 | Andersson et al. |
| 7,905,989 B2 | 3/2011 | Scherb et al. |
| 7,914,866 B2 | 3/2011 | Shannon et al. |
| 7,931,781 B2 | 4/2011 | Scherb et al. |
| 7,951,269 B2 | 5/2011 | Herman et al. |
| 7,955,549 B2 | 6/2011 | Noda |
| 7,959,764 B2 | 6/2011 | Ringer et al. |
| 7,972,475 B2 | 7/2011 | Chan et al. |
| 7,989,058 B2 | 8/2011 | Manifold et al. |
| 8,034,463 B2 | 10/2011 | Leimbach et al. |
| 3,051,629 A1 | 11/2011 | Pazdemik et al. |
| 8,075,739 B2 | 12/2011 | Scherb et al. |
| 8,092,652 B2 | 1/2012 | Scherb et al. |
| 8,118,979 B2 | 2/2012 | Herman et al. |
| 8,147,649 B1 | 4/2012 | Tucker et al. |
| 8,152,959 B2 | 4/2012 | Elony et al. |
| 8,196,314 B2 | 6/2012 | Munch |
| 8,216,427 B2 | 7/2012 | Klerelid et al. |
| 8,236,135 B2 | 8/2012 | Prodoehl et al. |
| 8,303,773 B2 | 11/2012 | Scherb et al. |
| 8,382,956 B2 | 2/2013 | Boechat et al. |
| 8,402,673 B2 | 3/2013 | Da Silva et al. |
| 8,409,404 B2 | 4/2013 | Harper et al. |
| 8,435,384 B2 | 5/2013 | Da Silva et al. |
| 8,440,055 B2 | 5/2013 | Scherb et al. |
| 8,445,032 B2 | 5/2013 | Topolkaraev et al. |
| 8,454,800 B2 | 6/2013 | Mourad et al. |
| 8,470,133 B2 | 6/2013 | Cunnane et al. |
| 8,506,756 B2 | 8/2013 | Denis et al. |
| 8,544,184 B2 | 10/2013 | Da Silva et al. |
| 8,580,083 B2 | 11/2013 | Boechat et al. |
| 8,758,569 B2 | 6/2014 | Aberg et al. |
| 8,771,466 B2 | 7/2014 | Denis et al. |
| 8,801,903 B2 | 8/2014 | Mourad et al. |
| 8,815,057 B2 | 8/2014 | Eberhardt et al. |
| 8,822,009 B2 | 9/2014 | Riviere et al. |
| 8,968,517 B2 | 3/2015 | Ramaratnam et al. |
| 8,980,062 B2 | 3/2015 | Karlsson et al. |
| 9,005,710 B2 | 4/2015 | Jones et al. |
| D734,617 S | 7/2015 | Seitzinger et al. |
| 9,095,477 B2 | 8/2015 | Yamaguchi |
| D738,633 S | 9/2015 | Seitzinger et al. |
| 9,382,666 B2 | 7/2016 | Ramaratnam et al. |
| 9,506,203 B2 | 11/2016 | Ramaratnam et al. |
| 9,580,872 B2 | 2/2017 | Ramaratnam et al. |
| 9,702,089 B2 | 7/2017 | Ramaratnam et al. |
| 9,702,090 B2 | 7/2017 | Ramaratnam et al. |
| 9,719,213 B2 | 8/2017 | Miller, IV et al. |
| 9,725,853 B2 | 8/2017 | Ramaratnam et al. |
| 2001/0018068 A1 | 8/2001 | Lorenzi et al. |
| 2002/0028230 A1 | 3/2002 | Eichhorn et al. |
| 2002/0060049 A1 | 5/2002 | Kanitz et al. |
| 2002/0061386 A1 | 5/2002 | Carson et al. |
| 2002/0098317 A1 | 7/2002 | Jaschinski et al. |
| 2002/0110655 A1 | 8/2002 | Seth |
| 2002/0115194 A1 | 8/2002 | Lange et al. |
| 2002/0125606 A1 | 9/2002 | McGuire et al. |
| 2002/0166646 A1 | 11/2002 | Drew |
| 2003/0024674 A1 | 2/2003 | Kanitz et al. |
| 2003/0056911 A1 | 3/2003 | Hermans et al. |
| 2003/0056917 A1 | 3/2003 | Jimenez |
| 2003/0070781 A1 | 4/2003 | Hermans et al. |
| 2003/0114071 A1 | 6/2003 | Everhart et al. |
| 2003/0159401 A1 | 8/2003 | Sorensson et al. |
| 2003/0188843 A1 | 10/2003 | Kanitz et al. |
| 2003/0218274 A1 | 11/2003 | Boutilier et al. |
| 2004/0013859 A1 | 1/2004 | Annis |
| 2004/0118531 A1 | 6/2004 | Shannon et al. |
| 2004/0123963 A1 | 7/2004 | Chen et al. |
| 2004/0126601 A1 | 7/2004 | Kramer et al. |
| 2004/0126710 A1 | 7/2004 | Hill et al. |
| 2004/0168784 A1 | 9/2004 | Duan et al. |
| 2004/0173333 A1 | 9/2004 | Hermans et al. |
| 2004/0234804 A1 | 11/2004 | Liu et al. |
| 2005/0016704 A1 | 1/2005 | Huhtelin |
| 2005/0069679 A1 | 3/2005 | Stelljes et al. |
| 2005/0069680 A1 | 3/2005 | Stelljes et al. |
| 2005/0098281 A1 | 5/2005 | Schulz et al. |
| 2005/0112115 A1 | 5/2005 | Khan |
| 2005/0123726 A1 | 6/2005 | Broering et al. |
| 2005/0130536 A1 | 6/2005 | Siebers et al. |
| 2005/0136222 A1 | 6/2005 | Hada et al. |
| 2005/0148257 A1 | 7/2005 | Hermans et al. |
| 2005/0150626 A1 | 7/2005 | Kanitz et al. |
| 2005/0166551 A1 | 8/2005 | Keane et al. |
| 2005/0241786 A1 | 11/2005 | Edwards et al. |
| 2005/0241788 A1 | 11/2005 | Baggot et al. |
| 2005/0252626 A1 | 11/2005 | Chen et al. |

(56) References Cited

U.S. PATENT DOCUMENTS

| | | |
|---|---|---|
| 2005/0280184 A1 | 12/2005 | Sayers et al. |
| 2005/0287340 A1 | 12/2005 | Morelli et al. |
| 2006/0005916 A1 | 1/2006 | Stelljes et al. |
| 2006/0013998 A1 | 1/2006 | Stelljes et al. |
| 2006/0019567 A1 | 1/2006 | Sayers |
| 2006/0083899 A1 | 4/2006 | Burazin et al. |
| 2006/0093788 A1 | 5/2006 | Behm et al. |
| 2006/0113049 A1 | 6/2006 | Knobloch et al. |
| 2006/0130986 A1 | 6/2006 | Flugge-Berendes et al. |
| 2006/0147505 A1 | 7/2006 | Tanzer et al. |
| 2006/0194022 A1 | 8/2006 | Boutilier et al. |
| 2006/0269706 A1 | 11/2006 | Shannon et al. |
| 2007/0020315 A1 | 1/2007 | Shannon et al. |
| 2007/0131366 A1 | 6/2007 | Underhill et al. |
| 2007/0137813 A1 | 6/2007 | Nickel et al. |
| 2007/0137814 A1 | 6/2007 | Gao |
| 2007/0170610 A1 | 7/2007 | Payne et al. |
| 2007/0240842 A1 | 10/2007 | Scherb et al. |
| 2007/0251659 A1 | 11/2007 | Fernandes et al. |
| 2007/0251660 A1 | 11/2007 | Walkenhaus et al. |
| 2007/0267157 A1 | 11/2007 | Kanitz et al. |
| 2007/0272381 A1 | 11/2007 | Elony et al. |
| 2007/0275866 A1 | 11/2007 | Dykstra |
| 2007/0295465 A1* | 12/2007 | Dyer ............... D21H 21/18 162/111 |
| 2007/0298221 A1 | 12/2007 | Vinson |
| 2008/0035289 A1 | 2/2008 | Edwards et al. |
| 2008/0076695 A1 | 3/2008 | Uitenbroek et al. |
| 2008/0156450 A1 | 7/2008 | Klerelid et al. |
| 2008/0199655 A1 | 8/2008 | Monnerie et al. |
| 2008/0245498 A1 | 10/2008 | Ostendorf et al. |
| 2008/0302493 A1 | 12/2008 | Boatman et al. |
| 2008/0308247 A1 | 12/2008 | Ringer et al. |
| 2009/0020248 A1 | 1/2009 | Sumnicht et al. |
| 2009/0056892 A1 | 3/2009 | Rekoske |
| 2009/0061709 A1 | 3/2009 | Nakai et al. |
| 2009/0104430 A1 | 4/2009 | Cordial |
| 2009/0205797 A1 | 8/2009 | Fernandes et al. |
| 2009/0218056 A1 | 9/2009 | Manifold et al. |
| 2010/0065234 A1 | 3/2010 | Klerelid et al. |
| 2010/0119779 A1 | 5/2010 | Ostendorf et al. |
| 2010/0224338 A1 | 9/2010 | Harper et al. |
| 2010/0230064 A1 | 9/2010 | Eagles et al. |
| 2010/0236034 A1 | 9/2010 | Eagles et al. |
| 2010/0239825 A1 | 9/2010 | Sheehan et al. |
| 2010/0272965 A1 | 10/2010 | Schinkoreit et al. |
| 2011/0027545 A1 | 2/2011 | Harlacher et al. |
| 2011/0180223 A1 | 7/2011 | Klerelid et al. |
| 2011/0189435 A1 | 8/2011 | Manifold et al. |
| 2011/0189442 A1 | 8/2011 | Manifold et al. |
| 2011/0206913 A1 | 8/2011 | Manifold et al. |
| 2011/0223381 A1 | 9/2011 | Sauter et al. |
| 2011/0253329 A1 | 10/2011 | Manifold et al. |
| 2011/0265967 A1 | 11/2011 | Van Phan |
| 2011/0290437 A1 | 12/2011 | Vogel et al. |
| 2011/0303379 A1 | 12/2011 | Boechat et al. |
| 2012/0144611 A1 | 6/2012 | Baker et al. |
| 2012/0152475 A1 | 6/2012 | Edwards et al. |
| 2012/0177888 A1 | 7/2012 | Escafere et al. |
| 2012/0244241 A1 | 9/2012 | McNeil |
| 2012/0267063 A1 | 10/2012 | Klerelid et al. |
| 2012/0297560 A1 | 11/2012 | Zwick et al. |
| 2013/0008135 A1 | 1/2013 | Moore et al. |
| 2013/0029105 A1 | 1/2013 | Miller et al. |
| 2013/0029106 A1 | 1/2013 | Lee et al. |
| 2013/0133851 A1 | 5/2013 | Boechat et al. |
| 2013/0150817 A1 | 6/2013 | Kainth et al. |
| 2013/0160960 A1 | 6/2013 | Hermans et al. |
| 2013/0209749 A1 | 8/2013 | Myangiro et al. |
| 2013/0248129 A1 | 9/2013 | Manifold et al. |
| 2013/0327487 A1 | 12/2013 | Espinosa et al. |
| 2014/0004307 A1 | 1/2014 | Sheehan |
| 2014/0041820 A1 | 2/2014 | Ramaratnam et al. |
| 2014/0041822 A1 | 2/2014 | Boechat et al. |
| 2014/0050890 A1 | 2/2014 | Zwick et al. |
| 2014/0053994 A1 | 2/2014 | Manifold et al. |
| 2014/0096924 A1 | 4/2014 | Rekokske et al. |
| 2014/0182798 A1 | 7/2014 | Polat et al. |
| 2014/0242320 A1 | 8/2014 | McNeil et al. |
| 2014/0272269 A1 | 9/2014 | Hansen |
| 2014/0272747 A1 | 9/2014 | Ciurkot |
| 2014/0284237 A1 | 9/2014 | Gosset |
| 2014/0360519 A1 | 12/2014 | George et al. |
| 2015/0059995 A1 | 3/2015 | Ramaratnam et al. |
| 2015/0102526 A1 | 4/2015 | Ward et al. |
| 2015/0129145 A1 | 5/2015 | Chou et al. |
| 2015/0211179 A1 | 7/2015 | Alias et al. |
| 2015/0241788 A1 | 8/2015 | Yamaguchi |
| 2015/0330029 A1* | 11/2015 | Ramaratnam ........... B32B 3/30 15/104.93 |
| 2016/0060811 A1 | 3/2016 | Riding et al. |
| 2016/0090692 A1 | 3/2016 | Eagles et al. |
| 2016/0090693 A1 | 3/2016 | Eagles et al. |
| 2016/0130762 A1 | 5/2016 | Ramaratnam et al. |
| 2016/0145810 A1 | 5/2016 | Miller, IV et al. |
| 2016/0159007 A1 | 6/2016 | Miller, IV et al. |
| 2016/0160448 A1 | 6/2016 | Miller, IV et al. |
| 2016/0185041 A1 | 6/2016 | Topolkaraev et al. |
| 2016/0185050 A1 | 6/2016 | Topolkaraev et al. |
| 2016/0273168 A1 | 9/2016 | Ramaratnam et al. |
| 2016/0273169 A1 | 9/2016 | Ramaratnam et al. |
| 2016/0289897 A1 | 10/2016 | Ramaratnam et al. |
| 2016/0289898 A1 | 10/2016 | Ramaratnam et al. |
| 2017/0044717 A1 | 2/2017 | Quigley |
| 2017/0056933 A1* | 3/2017 | Yamada .................. A47K 7/03 |
| 2017/0101741 A1 | 4/2017 | Sealey et al. |
| 2017/0167082 A1 | 6/2017 | Ramaratnam et al. |
| 2017/0226698 A1 | 8/2017 | LeBrun et al. |
| 2017/0233946 A1 | 8/2017 | Sealey et al. |
| 2017/0253422 A1 | 9/2017 | Anklam et al. |
| 2017/0268178 A1 | 9/2017 | Ramaratnam et al. |

FOREIGN PATENT DOCUMENTS

| | | |
|---|---|---|
| CN | 1268559 A | 10/2000 |
| CN | 1377405 A | 10/2002 |
| CN | 2728254 Y | 9/2005 |
| DE | 4242539 A1 | 8/1993 |
| EP | 0097036 A2 | 12/1983 |
| EP | 0496524 A1 | 7/1992 |
| EP | 0979895 A1 | 2/2000 |
| EP | 1911574 A1 | 1/2007 |
| EP | 1339915 B1 | 7/2007 |
| EP | 2123826 A2 | 5/2009 |
| GB | 946093 A | 1/1964 |
| JP | 2013208298 A | 10/2013 |
| JP | 2014213138 A | 11/2014 |
| WO | 96/06223 A1 | 2/1996 |
| WO | 9922059 A1 | 5/1999 |
| WO | 200382550 A2 | 10/2003 |
| WO | 200445834 A1 | 6/2004 |
| WO | 2007070145 A1 | 6/2007 |
| WO | 2008019702 A1 | 2/2008 |
| WO | 2009006709 A1 | 1/2009 |
| WO | 2009061079 A1 | 5/2009 |
| WO | 2009067079 A1 | 5/2009 |
| WO | 2011028823 A1 | 3/2011 |
| WO | 2012003360 A2 | 1/2012 |
| WO | 2013024297 A1 | 2/2013 |
| WO | 2013136471 A1 | 9/2013 |
| WO | 2014/022848 A1 | 2/2014 |
| WO | 201500755 A1 | 1/2015 |
| WO | 2015/176063 A1 | 11/2015 |
| WO | 2016/022880 A1 | 2/2016 |
| WO | 2016/077594 A1 | 5/2016 |
| WO | 2016/086019 A1 | 6/2016 |
| WO | 2016/090242 A1 | 6/2016 |
| WO | 2016/090364 A1 | 6/2016 |
| WO | 2016085704 A1 | 6/2016 |
| WO | 2017066465 A1 | 4/2017 |

(56) References Cited

FOREIGN PATENT DOCUMENTS

| WO | 2017066656 A1 | 4/2017 |
| WO | 2017139786 A1 | 8/2017 |

OTHER PUBLICATIONS

International Written Opinion of PCT/US17/60608 dated Jan. 5, 2018.
Supplementary European Search Report of EP15792709 dated Nov. 13, 2017.
International Search Report for PCT/US16/56871 dated Jan. 12, 2017.
Written Opinion of International Searching Authority for PCT/US16/56871 dated Jan. 12, 2017.
International Search Report for PCT/US2016/057163 dated Dec. 23, 2016.
Written Opinion of International Searching Authority for PCT/US2016/057163 dated Dec. 23, 2016.
International Search Report for PCT/US2017/029890 dated Jul. 14, 2017.
Written Opinion of International Searching Authority for PCT/US2017/029890 dated Jul. 14, 2017.
International Search Report for PCT/US2017/032746 dated Aug. 7, 2017.
Written Opinion of International Searching Authority for PCT/US2017/032746 dated Aug. 7, 2017.
International Search Report for PCT/US17/17705 dated Jun. 9, 2017.
Written Opinion of International Searching Authority for PCT/US17/17705 dated Jun. 9, 2017.
Written Opinion of International Searching Authority for PCT/US15/62483 dated May 6, 2016.
International Search Report for PCT/US15/63986 dated Mar. 29, 2016.
Written Opinion of International Searching Authority for PCT/US15/63986 dated Mar. 29, 2016.
International Search Report for PCT/US15/64284 dated Feb. 11, 2016.
Written Opinion of International Searching Authority for PCT/US15/64284 dated Feb. 11, 2016.
International Search Report for PCT/US13/53593 dated Dec. 30, 2013.
Written Opinion of International Searching Authority for PCT/US13/53593 dated Dec. 30, 2013.
International Search Report for PCT/US15/31411 dated Aug. 13, 2015.
Written Opinion of International Searching Authority for PCT/US15/31411 dated Aug. 13, 2015.
International Search Report for PCT/US15/60398 dated Jan. 29, 2016.
Written Opinion of International Searching Authority for PCT/US15/60398 dated Jan. 29, 2016.
International Search Report for PCT/US15/62483 dated May 6, 2016.
"TAPPI T-204 cm-07 Standard—2007"—TAPPI 2007 (4 pages).

* cited by examiner

FLUSHABLE WIPE AND METHOD OF FORMING THE SAME

CROSS-REFERENCE TO RELATED APPLICATION

This application is a continuation-in-part of U.S. patent application Ser. No. 14/715,350, filed May 18, 2015, and entitled "FLUSHABLE WIPE AND METHOD OF FORMING THE SAME", which in turn claims the benefit of U.S. Provisional Application No. 61/994,563 filed May 16, 2014, and entitled "WIPE AND METHOD OF FORMING THE SAME," and the entire contents of these applications are incorporated by reference herein.

FIELD OF THE INVENTION

The present invention is directed to wipes such as disposable, dispersible, hygienic wipes.

BACKGROUND

In recent years, a growing number of people have begun to use value added consumer disposable items like facial cleaning wipes, moist towelettes, personal hygiene wipes, and time-saving products like household cleaning wipes. The market for wipes is forecast to rise significantly in the coming years.

Once dominated by baby care, the wipes market has branched out into applications targeted for specific uses like personal hygiene and household cleansing. Personal care wipes currently represent approximately 60% of the North American market for wipes and is inclusive of baby wipes, various targeted personal hygiene cleansing wipes (hands, face, wounds, flushable adult wipes), feminine hygiene, and adult incontinence. Household wipes currently represent approximately 25% of the market and are inclusive of targeted cleansing wipes for the kitchen, bathroom, windows, and even automobiles. Industrial wipes represent the remaining approximately 15% of the market and are used for industrial equipment cleaning.

A key consumer demand is for greener or more eco-friendly wipe products. This necessitates developing biodegradable products with minimal environmental footprint through all levels of the supply chain, including raw materials, packaging, transportation, and overall manufacturing operations.

"Flushability" has become a critical issue for wipes manufacturers as well. Wastewater treatment facilities have been focusing their attention on wipes as they are clogging piping and pumps at the treatment plants. INDA has been working with wipes manufacturers, wastewater treatment facilities and local government officials to address this growing issue.

Utilization of the appropriate technology and fiber sources to create wipe products that are low cost, eco-friendly, and of high quality are therefore mandatory for success in today's marketplace.

Currently available flushable wipe products are not truly flushable because they do not disperse well in all conditions that wipes encounter in the household toilet/septic systems. Most of these products are size-based flushable wipes and pass through plumbing systems without breaking down into smaller pieces or fiber clusters. As a result, even though they pass through the piping systems immediately after flushing, they often plug up the sewage systems and the effluent clarifier's controlled by the city/municipal systems. In addition, the fibers used in the manufacture of these types of products are not all natural fibers. Almost every flushable product available has a significant amount of synthetic fibers, such as polyethylene, polypropylene, or polyester, in the form of single component or bicomponent fibers. Almost all products that are claimed as flushable wipes may pass the INDA flushability guidelines but are not truly flushable because they do not disperse adequately to pass through smaller pipes and other types of restrictions in sewage treatment systems.

SUMMARY OF THE INVENTION

An object of the present invention is to provide a true flushable wipe that disperses when flushed and does not plug up city/municipal sewage systems (i.e., the wipe is septic safe).

Another object of the present invention is to provide a flushable wipe that is biodegradable.

Another object of the present invention is to provide a flushable wipe that utilizes an ion triggered binder to allow the wipe to be pre-moistened without losing its functional strength properties while still dispersing when submerged in water.

This trigger component is a controlled concentration of salt in the binder or wetting solution that insolubilizes the binder additives and allows it to function as an adhesive for the substrate. When the controlled concentration of salt is diluted, the binder becomes soluble allowing the substrate to disperse. Without being bound by theory, it is believed that the salt also prevents strength additives in the substrate from solubilizing enhancing the strength of the substrate while in the wetting solution.

In embodiments, the flushable wipe of the present invention may be single ply. In other embodiments, the flushable wipe may comprise two or more plies.

The present invention also encompasses a method of manufacturing such flushable wipes and an apparatus for manufacturing such flushable wipes.

The natural fibers of the wipe may comprise fibers of the type selected from the group consisting of: softwood fibers, hardwood fibers, elephant grass, nettle, buntal, buri, soybean protein, milvet milk, abaca, bagasse, bamboo, coir, cotton, flax, linen, hemp, jute, kapok, kenaf, pina, raffia, ramie, sisal, oxidized natural fibers and combinations thereof. The natural fibers may be or may include alternate natural fibers of the type selected from the group consisting of: abaca, bamboo, coir, flax, linen, kapok, pina, raffia, ramie, sisal, nettle, buntal, buri, cotton, kenaf, elephant grass, jute, hemp, bagasse fibers and combinations thereof.

If synthetic fibers are incorporated, the average fiber length of the wipe must remain below 5 mm and more preferably 4 mm. The synthetic fibers, which may be or may include semi-synthetic fibers, may comprise fibers of the type selected from the group consisting of: acrylic, aramid, para-aramid, meta-aramid, modacrylic, nylon, olefin, polyester, polyethylene, ultra-high molecular weight polyethylene, polyester-polyurethane copolymer, polyvinyl alcohol, polyvinyl chloride, poly(p-phenylene-2,6-benzobisoxazole), polypropylene, ethylene vinyl alcohol and combinations thereof, and/or may comprise semisynthetic fibers of the type selected from the group consisting of: regenerated cellulose, rayon, lyocell, polylactic acid, polyvinyl alcohol and combinations thereof.

A flushable wipe according to an exemplary embodiment of the present invention has at least one of the following properties: a basis weight below 90 gsm, a machine direction tensile strength within the range of 30 N/m to 250 N/m, or preferably a machine direction tensile strength within the range of 50 N/m to 150 N/m, a cross direction tensile strength within the range of 30 N/m to 250 N/m, or preferably a cross direction tensile strength within the range of 50 N/m to 150 N/m, and a thickness within the range of 300 to 1500 microns, preferably a thickness within the range of 400 to 1250 microns.

The flushable wipe may be comprised of one or more of the following combinations: a combination of softwood fibers and alternate natural fibers; a combination of softwood fibers and modified rayon fibers; a combination of softwood fibers and renewable polymeric fibers; a combination of softwood fibers and water based polyvinyl alcohol (PVA) fibers; a combination of softwood fibers, renewable polymeric fibers and polyvinyl alcohol (PVA) fibers; and a combination of softwood fibers, modified rayon fibers, renewable polymeric fibers, water-based polyvinyl alcohol (PVA) fibers and alternate natural fibers.

A slurry from which the flushable wipe is formed may comprise additives, enzymes, and/or fillers. The additives may comprise additives of the type selected from the group consisting of: urea formaldehyde, melamine formaldehyde, poly amide poly amine epichlorohydrin, polyethlyenimine, starch, starch derivatives, aldehyde functionalized starches, chitosan, aldehyde functionalize polyacrylamides, glyoxalated polyacrylamide, glyoxalated copolymer, carboxyl methyl cellulose, polyvinyl alcohol, polyvinyl acetate, polyvinyl amine, polyamide resins, polyacrylamide resins, galactomannan gums, acrylic emulsions, styrene-butadiene latexes, vinyl acetate polymers, ethylene-vinyl acetate copolymers, vinyl chloride polymers, vinylidene chloride polymers, vinyl chloride-vinylidene copolymers, acrylo-nitrile copolymers, ethylene-acrylic copolymers, latex emulsions, acrolein copolymers and combinations thereof. The enzyme may comprise, for example, oxidoreductase enzymatic systems. The fillers may comprise, for example, at least one of calcium carbonate particles, clay particles or talc particles. The wipe may also include filler material, such as at least one of super absorbent polymers and encapsulated polymers.

The flushable wipe may include a binder. The binder may be of a type selected from the group consisting of: poly (vinyl) alcohol, poly(vinyl) acetate, poly (ethylene) (vinyl) alcohols, poly (ethylene) (vinyl) acetate, copolymers of vinyl acetate-ethylene, starch based chemistries and combinations thereof. The binder may further comprise a cross-linking agent such as N-methylolacrylamide, ion sensitive polymers, or a trigger chemistry, such as NaCl, NaBr, KCl, NH4Cl, Na2SO4, AnCl2, CaCl2, MgCl2, MgSO4, NaNO3, NaSO4CH3, BNa3O3, NaB4O7 or combinations thereof. The binder may further contain a pH buffering agent. The two or more plies of the wipe may be held together by embossments.

In embodiments, the flushable wipe also comprises a cleansing solution and/or a wetting/cleaning solution. The cleansing solution may contain a trigger chemistry in concentration of 0.1% to 10% by weight of a mono or divalent salt. The mono or divalent salt is selected from NaCl, NaBr, KCl, NH4Cl, Na$_2$SO$_4$, AnCl$_2$, CaCl$_2$), MgCl$_2$, MgSO$_4$, NaNO$_3$, NaSO$_4$CH$_3$, BNa$_3$O$_3$, NaB$_4$O$_7$ or combinations thereof. A cleansing solution may include glycol based cross-linking chemistry, anhydrides and epoxy groups, cyclo-dextrins adapted to release fragrances, and/or at least one of aloe or shea butter. The cleansing solution may be present in the amount of 40% to 80% by weight. A wetting/cleaning solution may include purified water and a combination of one or more of the following: humectants, preservatives, moisturizers, surfactants, chelating agents, pH buffer and aromatic compounds.

The resulting flushable wipe desirably has a basis weight within the range of 20 gsm to 100 gsm.

In another exemplary embodiment, the wipe may have at least one of the following properties: a basis weight below 90 gsm, a machine direction tensile strength within the range of 30 N/m to 250 N/m, or preferably a machine direction tensile strength within the range of 50 N/m to 150 N/m, According to an exemplary embodiment of the present invention, a single or multi-ply flushable and dispersible wet wipe includes a wet laid fibrous web imprinted using a structuring fabric, a binder composition comprising poly (vinyl) alcohol, poly(vinyl) acetate, poly (ethylene) (vinyl) alcohols, poly (ethylene) (vinyl) acetate, copolymers of vinyl acetate-ethylene, or combinations thereof, and one or more additives. In an exemplary embodiment, the fibrous web is wetted by a wetting solution comprising 0.1% to about 10% by weight of one of the following: (1) boric acid; and (2) boric acid and a mono or divalent salt.

Other features and advantages of embodiments of the invention will become readily apparent from the following detailed description, the accompanying drawings and the appended claims.

BRIEF DESCRIPTION OF THE DRAWINGS

Exemplary embodiments of the present invention will be described with references to the accompanying figures, wherein.

DETAILED DESCRIPTION

The present invention is directed to a flushable and dispersible wipe composed of natural fibers or a blend of natural fibers (which may be or include alternative natural fibers) and long synthetic fibers (which may be or include semi-synthetic fibers). For the purposes of the present disclosure, the term "long fiber" is intended to mean fibers having a length of at least 1 mm, preferably within the range of 1 mm and 4.9 mm, more preferably within the range of 3 mm and 4.9 mm. Also, for the purposes of the present disclosure, the term "flushable" is intended to mean that the wipe is able to be disposed of through sanitation fixtures, such as toilets, without clogging or otherwise interfering with the disposal process. The current measure of flushability is set by the 3rd edition of the INDA/EDANA Flushability Guidelines (Guidance Document for Assessing Flushability of Nonwoven Disposable Products (June 2013)). A wipe is considered "dispersible" if it passes the Slosh Box Disintegration Test set forth in INDA FG502. Unless otherwise specified, for the purposes of the present invention, weight percentages are given relative to the dry weight of the final product (i.e, prior to application of lotions or other post formation additives).

Figure 1:
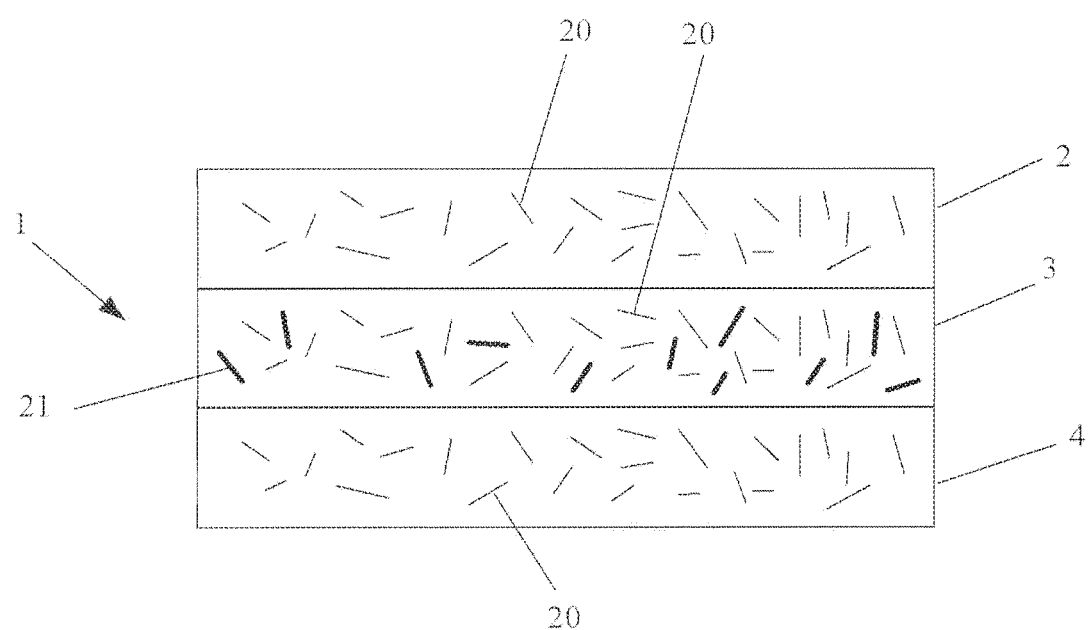
FIG. 1 is a schematic diagram of a three layer ply of a wipe formed by a wet laid process in accordance with an exemplary embodiment of the present invention.

FIG. 1 shows a three layer ply of a wipe, generally designated by reference number 1, according to an exemplary embodiment of the present invention. The wipe 1 has external layers 2 and 4 as well as an internal, core layer 3. External layers 2 and 4 are composed primarily of natural fibers 20, and in an exemplary embodiment the external layers 2 and 4 are made up of 50% to 100% by weight natural fibers. (The remaining fibers can be synthetic or semisynthetic fibers.) In an exemplary embodiment, the external layers 2 and 4 are made up of 100% by weight natural fibers. The core layer 3 is composed of water-formed or foam-formed fiber blend of natural fibers 20 and long synthetic fibers 21 or 100% natural fibers. The synthetic fibers 21 are non-thermoplastic fibers. In an exemplary embodiment, the core layer 3 is made up of 25% to 75% by weight natural fibers and 1% to 75% by weight long synthetic fibers. (The remaining fibers can be short synthetic or semisynthetic fibers.) In an exemplary embodiment, the core layer 3 is made of 100% by weight natural fibers. The basis weight of the wipe 1 is within the range of 20 gsm to 100 gsm, and in an exemplary embodiment has a basis weight of 50 gsm. The average fiber length of the long synthetic fibers that are used in wipe 1 is, in embodiments, less than 5 mm, and may be more preferably less than 4 mm.

The wipe 1 may be produced using a single layered headbox wherein the above mentioned natural and synthetic fibers, or combinations thereof may be used in the forming section. Alternatively, wipe 1 may be produced using a stratified headbox to form multiple layers simultaneously.

The natural fibers/alternate natural fibers 20 used to form the wipe 1 may be composed of natural cellulose fibers derived from, for example, softwood, hardwood, kenaf, elephant grass, esparto grass, sisal, abaca, jute, hemp, kemp, bagasse, cotton linters, soybean protein, milvet milk, abaca, bamboo, coir, flax, linen, kapok, pina, raffia, ramie, sisal, nettle, buntal, buri, other lignaceous and cellulose fibers, or other oxidized natural fibers that increase acid group content greater than 5.5 meq/100 g (meq=milliequivalents of solute), or combinations thereof. For example, the combination of natural fibers that are used may be a combination of softwood and hardwood fibers, or a combination of softwood fibers and alternate natural fibers.

The synthetic fibers 21 if used to form the core layer 3 may be, for example, rayon fibers, renewable polymeric fibers, water-based polyvinyl alcohol (PVA) fibers, acrylic, aramid, Twaron®, Kevlar®, Technora®, Nomex®, microfiber, modacrylic, nylon, olefin, polyester, polyethylene, Dyneema®, Spectra®, spandex, vinylon, vinyon, Zylon®, polypropylene, or ethylene einyl alcohol, or combinations thereof. The semi-synthetic fibers that can be used to form the core layer 3 may be, for example, modified rayon fibers, regenerated cellulose (from any source such as bamboo, wood, modal, acetate, diacetate, or triacetate), polylactic acid, or polyvinyl alcohol or combinations thereof. Thus, the core layer 3 may include, for example, one or more natural fibers, such as softwood fibers, and one or more of these synthetic or semisynthetic fibers.

If modified rayon fibers are used as the synthetic fibers 21, the modified rayon fibers may be composed of viscose rayon, lyocell (e.g., Tencel®, manufactured by Lenzing AG of Lenzing, Austria), or combinations thereof and may have an inclusion rate within the range of 10% to 50% by weight of the entire tissue, and preferably 25% by weight of the entire tissue. The modified rayon fibers have a length within the range of 1 to 4.9 mm. The modified rayon fibers may be shaped fibers, such as, for example, fibers having multi-lobal or star-shaped cross sections.

If water-based PVA fibers are used as the synthetic fibers 21, the water-based PVA fibers may be added at an inclusion rate of 10% to 50% by weight of the entire tissue, and preferably 25% by weight of the entire tissue. The water-based PVA fibers have a length within the range of 3 mm to 4.9 mm, and may be shaped fibers, such as, for example, fibers having multi-lobal or star-shaped cross sections.

If renewable polymeric fibers are used as the synthetic fibers 21, the renewable polymeric fibers may be composed of poly(lactic acid) (PLA) and may have an inclusion rate within the range of 10% to 50% by weight of the entire tissue, and preferably 25% by weight of the entire tissue. The renewable polymeric fibers have a length within the range of 3 mm to 4.9 mm. The renewable polymeric fibers may be shaped fibers, such as, for example, fibers having multi-lobal or star-shaped cross sections.

Wet-end additives may be included in the layers of the wipe 1. In this regard, as known in the art, pulp mixes are subjected to a dilution stage in which water is added to the mixes so as to form a slurry. After the dilution stage but prior to reaching the headbox, each of the pulp mixes are dewatered to obtain a thick stock of about 95% water. In an exemplary embodiment of the invention, wet end additives are introduced into the thick stock pulp mixes of all layers, and in an exemplary embodiment the wet end additives may only be introduced into the thick stock pulp mixes of only the external layers. Suitable wet-end additives include temporary wet strength additives, such as, for example, water-based PVA, glyoxalated polyacrylamide (commonly known as GPAM), carboxyl methyl cellulose (CMC), and combinations thereof, such as a combination of GPAM and CMC. If GPAM is used as the wet-end additive, the GPAM may be present at concentrations ranging from 0.01% to 4% of the weight of the fibers of the wipe 1, and in an exemplary embodiment is present at a concentration of 0.5% of the weight of the fibers of the wipe 1. If carboxyl methyl cellulose is used as the wet-end additive, the carboxyl methyl cellulose may be present at concentrations ranging from 0.01% to 1% of the weight of fibers of the wipe 1, and in an exemplary embodiment is present at a concentration of 0.25% of the weight of fibers of the wipe 1.

Enzymes may also be added to the slurry as a wet-end additive to refine, de-ink and/or bleach recycled pulp. Such enzymes may be present at concentrations ranging from 0.1% to 2% of the weight of fibers. An example of a suitable enzyme is oxidoreductase, which requires a small dose of hydrogen peroxide initiator or ammonium per sulfate.

In an exemplary embodiment, a dry strength additive is added to the thick stock mix for at least one of the layers of the tissue. The dry strength additive may be, for example, amphoteric starch, added in a range of about 1 kg/ton to 15 kg/ton to the thick stock mix.

As an alternative or in addition to the use of wet end additives, the wipe of the present invention may be treated with topical or surface deposited additives. Examples of surface deposited additives include temporary wet strength additives such as GPAM and/or CMC. The temporary wet strength additive may be sprayed directly on the wipe basesheet during the converting process with an add-on up to 1% to 2% of the weight of the fibers of the wipe 1.

Other examples of surface deposited additives include softeners for increasing fiber softness and skin lotions. Examples of topical softeners include but are not limited to quaternary ammonium compounds, including, but not limited to, the dialkyldimethylammonium salts (e.g. ditallowdimethylammonium chloride, ditallowdimethylammonium methyl sulfate, di(hydrogenated tallow)dimethyl ammonium chloride, etc.). Another class of chemical softening agents include the well-known organo-reactive polydimethyl siloxane ingredients, including amino functional polydimethyl siloxane. zinc stearate, aluminum stearate, sodium stearate, calcium stearate, magnesium stearate, spermaceti, and steryl oil. The softener additive may be applied to the basesheet by, for example, spraying, roll coating/anilox roll set up or flexographic/gravure roll coating the wipes when they are a wet laid asset or after the wipes are dried but before wetting solution is added to the package.

In addition to the above, other additives can be incorporated into the slurry prior to deposition onto the forming surface, sprayed onto the web during the wet-laid process or added during the plying step after the web has fully dried. In embodiments, the additives can be added in an amount up to 5% of the weight of fibers of the wipe 1.

The additives can be one or a combination of the following: urea formaldehyde, melamine formaldehyde, poly amide poly amine epichlorohydrin, polyethlyenimine, starch and starch derivatives, aldehyde functionalized starches, chitosan, aldehyde functionalize polyacrylamides, glyoxalated polyacrylamide, glyoxalated copolymer, carboxyl methyl cellulose, polyvinyl alcohol, polyvinyl acetate, polyvinyl amine, polyamide resins, polyacrylamide resins, galactomannan gums such as guar guam and locus bean gum, acrylic emulsions, styrene-butadiene latexes, vinyl acetate polymers, ethylene-vinyl acetate copolymers, vinyl chloride polymers, vinylidene chloride polymers, vinyl chloride-vinylidene copolymers, acrylo-nitrile copolymers, ethylene-acrylic copolymers, latex emulsions, and acrolein copolymers. In embodiments, when added to the slurry, these additives can be added at a concentration ranging from 0.1 to 4% of the weight of fibers, more preferably about 0.5% of the weight of fibers.

The additives can also be a combination of the following: starch and starch derivatives, aldehyde functionalized starches, chitosan, aldehyde functionalize polyacrylamides, glyoxalated polyacrylamide, glyoxalated copolymers, carboxyl methyl cellulose, polyvinyl alcohol, polyvinyl acetate, polyvinyl amine, polyamide resins, polyacrylamide resins, galactomannan gums such as guar guam and locus bean gum, acrylic emulsions, styrene-butadiene latexes, vinyl acetate polymers, ethylene-vinyl acetate copolymers, vinyl chloride polymers, vinylidene chloride polymers, vinyl chloride-vinylidene copolymers, acrylo-nitrile copolymers, ethylene-acrylic copolymers, latex emulsions, and acrolein copolymers. In embodiments, when added to the slurry, these additives can be added at a concentration ranging from 0.1 to 4% of the weight of fibers of the wipe 1, more preferably about 0.5% of the weight of fibers of the wipe 1.

The additives can alternatively be one or a combination of the following: starch and starch derivatives, aldehyde functionalized starches, chitosan, aldehyde functionalize polyacrylamides, glyoxalated polyacrylamide, glyoxylated copolymers, carboxyl methyl cellulose, polyvinyl alcohol, polyvinyl acetate, polyvinyl amine, polyamide resins, polyacrylamide resins, galactomannan gums such as guar guam and locus bean gum. In embodiments, when added to the slurry these additives can be added at a concentration ranging from 0.1 to 4% of the weight of fibers of the wipe 1, more preferably about 0.5% of the weight of fibers of the wipe 1.

The additives can alternatively be one or a combination of the following: starch and starch derivatives, aldehyde functionalized starches, chitosan, aldehyde functionalize polyacrylamides, glyoxalated polyacrylamide, glyoxylated copolymers, carboxyl methyl cellulose, polyvinyl alcohol, polyvinyl acetate, polyvinyl amine, polyamide resins, and polyacrylamide resins. In embodiments, when added to the slurry these additives can be added at a concentration ranging from 0.1 to 4% of the weight of fibers of the wipe 1, more preferably about 0.5% of the weight of fibers of the wipe 1.

A cleansing solution may be topically applied to the wipe. The cleaning solution is preferably applied to the wipes after being packaged but prior to the package being sealed. Examples of cleansing solutions include glycol-based cross-linking chemistry including anhydrides and epoxy groups, cyclo-dextrins with the ability to release fragrances, aloe (such as Aloe E) and shea butter. The cleansing solution can be composed of 85-99.9% water with the remainder being mono or divalent salts, preservative, humectants, moisturizers, pH buffers, surfactants, or aromatic compounds. The mono or divalent salts is selected from NaCl, NaBr, KCl, $NH_4Cl$, $Na_2SO_4$, $ZnCl_2$, $CaCl_2$), $MgCl_2$, $MgSO_4$, $NaNO_3$, $NaSO_4CH_3$, $BNa_3O_3$, $NaB_4O_7$ or combinations thereof. In embodiments, the aloe or shea butter may be applied in a concentration of up to 0.5% of the cleansing solution. In embodiments, the wet wipe may contain as much as 40% to 90% by weight of cleansing solution in the final product, and more preferably 70% by weight of cleansing solution in the final product.

Fillers may also be added to the slurry at addition rates of 0.1% to 1% of the weight of the fibers of the wipe 1, more preferably about 0.5% by weight of fibers of the wipe 1. Fillers may be, for example, calcium carbonate particles, clay particles and/or talc particles. Fillers may also be superabsorbent polymers or encapsulated polymers.

The absorbent products or structures that are used for each of the webs for the one or more plies can be manufactured by any known or later-discovered wet-laid method that uses water to form a web. Examples of some known wet-laid technologies that may be used to form a cellulosic (or other natural or synthetic fiber type) web include Through Air Drying (TAD), Uncreped Through Air Drying (UCTAD), Conventional Wet Crepe (CWC), Conventional Dry Crepe (CDC), Advanced Tissue Molding System (ATMOS), NTT, and ETAD.

The Through Air Drying (TAD) and Uncreped Through Air Drying (UCTAD) processes are wet-laid technologies that avoid compaction of the web during drying and thereby produce absorbent products of superior thickness and absorbency when compared to absorbent products of similar basis weight and material inputs that are produced using the CWC or the CDC process. Other wet-laid processes, such as ATMOS, ETAD, and NTT, utilizes some pressing to dewater the web, or a portion of the web, resulting in absorbent products with absorbent capacities that correlate to the amount of pressing utilized when all other variables are the same. Some wet-laid processes are discussed below.

Wet-Laid Processes

Tissue papermaking is a complex process where specific control over product quality attributes is critical. Arguably, the most critical pieces of equipment used to control these quality attributes are the fabrics utilized in the papermaking machines. The various papermaking machine technologies are conventional dry crepe, through air drying (TAD), or hybrid technologies such as Valmet NTT (Valmet Corp., Helsinki, Finland), Georgia Pacific's ETAD (Georgia Pacific LLC, Atlanta, Ga.), or Voith's ATMOS process (Voith GmbH, Heidenheim, Germany). All these technologies utilize fabrics at various stages in the process to influence tissue web properties and overall asset productivity.

The predominant manufacturing method for making a tissue web is the conventional dry crepe process. The major steps of the conventional dry crepe process involve stock preparation, forming, pressing, drying, creping, calendering (optional), and reeling the web.

The first step of stock preparation involves selection, blending, mixing, and preparation of the proper ratio of wood, plant, or synthetic fibers along with chemistry and fillers that are needed in the specific tissue grade. This mixture is diluted to over 99% water in order to allow for an even fiber formation when deposited from the machine headbox into the forming section. There are many types of forming sections used in conventional papermaking (inclined suction breast roll, twin wire C-wrap (with a solid or suction forming roll), twin wire S-wrap, suction forming roll, and Crescent formers) but all are designed to retain the fiber, chemical, and filler recipe while allowing the water to drain from the web. In order to accomplish this, fabrics, referred to as "forming fabrics," are utilized.

Forming fabrics are woven structures that utilize monofilaments (yarns, threads) composed of synthetic polymers (usually polyethylene, polypropylene, or nylon). The forming fabric has two surfaces: the sheet side and the machine or wear side. The wear side is in contact with the elements that support and move the fabric and are thus prone to wear. To increase wear resistance and improve drainage, the wear side of the fabric has larger diameter monofilaments compared to the sheet side. The sheet side has finer yarns to promote fiber and filler retention on the fabric surface.

In order to control other properties such as: fabric stability, life potential, drainage, fiber support, and clean-ability, different weave patterns are utilized. Generally, forming fabrics are classified by the number of layers utilized in their construction. There are three basic styles of forming fabrics: single layer, double layer, and triple layer. A single layer fabric is composed of one CD (shute) and one MD (warp) yarn system. The main problem of single layer fabrics is lack of dimensional stability. The double layer forming fabric has one layer of warp yarns and two layers of shute yarns. This multilayer fabric is generally more stable and resistant to stretching. Triple layer fabrics have two separate single layer fabrics bound together by separated yarns called binders. Usually the binder fibers are placed in cross direction but also can be oriented in the machine direction. Triple layer fabrics have further increased dimensional stability, wear potential, drainage, and fiber support than single or double layer fabrics.

The manufacturing of forming fabrics comprises the following operations: weaving, initial heat setting, seaming, final heat setting, and finishing. The fabric is made in a loom using two interlacing sets of monofilaments (or threads or yarns). The longitudinal threads are called the warp and the transverse threads are called shute threads. After weaving, the forming fabric is heated to relieve internal stresses to enhance dimensional stability of the fabric. The next step in manufacturing is seaming. This step converts the flat woven fabric into and endless forming fabric by joining the two MD ends of the fabric. After seaming, the final heat setting is applied to stabilize and relieve the stresses in the seam area. The final step in the manufacturing process is finishing, where the fabric is cut to width and sealed.

There are several parameters and tools used to characterize the properties of the forming fabric: mesh and count, caliper, frames, plane difference, open area, air permeability, void volume and distribution, running attitude, fiber support, drainage index, and stacking. None of these parameters can be used individually to precisely predict the performance of a forming fabric on a paper machine, but together the expected performance and sheet properties can be estimated.

In a conventional process, after web formation and drainage (to around 35% solids) in the forming section (assisted by centripetal force around the forming roll, and vacuum boxes in several former types), the web is transferred to a press fabric upon which the web is pressed between a rubber or polyurethane covered suction pressure roll and Yankee dryer. The press fabric is a permeable fabric designed to uptake water from the web as it is pressed in the press section. It is composed of large monofilaments or multi-filamentous yarns, needled with fine synthetic batt fibers to form a smooth surface for even web pressing against the Yankee dryer.

After pressing the sheet, between a suction pressure roll and a steam heated cylinder (referred to as a Yankee dryer), the web is dried from up to 50% solids to up to 99% solids using the steam heated cylinder and hot air impingement from an air system (air cap or hood) installed over the steam cylinder. The sheet is then creped (i.e. removed) from the steam cylinder using a steel or ceramic doctor blade. This is a critical step in the conventional dry crepe process. The creping process greatly affects softness as the surface topography is dominated by the number and coarseness of the crepe bars (finer crepe is much smoother than coarse crepe). Some thickness and flexibility is also generated during the creping process. If the process is a wet crepe process, the web must be conveyed between dryer fabrics through steam heated after-dryer cans to dry the web to the required finished moisture content. After creping, the web is optionally calendered and reeled into a parent roll and ready for the converting process.

The through air dried (TAD) process is another manufacturing method for making a tissue web. The major steps of the through air dried process are stock preparation, forming, imprinting, thermal pre-drying, drying, creping, calendering (optional), and reeling the web. The stock preparation and forming steps are similar to conventional dry creping.

Rather than pressing and compacting the web, as is performed in conventional dry crepe, the web undergoes the steps of imprinting and thermal pre-drying. Imprinting is a step in the process where the web is transferred from a forming fabric to a structured fabric (or imprinting fabric) and subsequently pulled into the structured fabric using vacuum (referred to as imprinting or molding). This step imprints the weave pattern (or knuckle pattern) of the structured fabric into the web. This imprinting step has a tremendous effect on the softness of the web, both affecting smoothness and the bulk structure. The design parameters of the structured fabric (weave pattern, mesh, count, warp and weft monofilament diameters, caliper, air permeability, and optional over-laid polymer) are, therefore, critical to the development of web softness. The manufacturing method of an imprinting fabric is similar to a forming fabric, except for an additional step if an overlaid polymer is utilized. These type of fabrics are disclosed in patents such as U.S. Pat. Nos. 5,679,222; 4,514,345; 5,334,289; 4,528,239 and 4,637,859, hereby incorporated by reference. Essentially, fabrics produced using these methods result in a fabric with a patterned resin applied over a woven substrate. The benefit is that resulting patterns are not limited by a woven structure and can be created in any desired shape to enable a higher level of control of the web structure and topography that dictate web quality properties.

Another manufacturing method for producing structuring or imprinting fabrics is disclosed in U.S. Pat. No. 8,980,062 and U.S. Patent Application Publication No. US 2010/0236034. The process involves spirally winding strips of polymeric material, such as industrial strapping or ribbon material, and adjoining the sides of the strips of material using ultrasonic, infrared, or laser welding techniques to produce an endless belt. Optionally, a filler or gap material can be placed between the strips of material and melted using the aforementioned welding techniques to join the strips of materials. The strips of polymeric material are produced by an extrusion process from any polymeric resin such as polyester, polyamide, polyurethane, polypropylene, or polyether ether ketone resins. The strip material can also be reinforced by incorporating monofilaments of polymeric material into the strips during the extrusion process or by laminating a layer of woven polymer monofilaments to the non-sheet contacting surface of a finished endless belt composed of welded strip material. The endless belt can have a textured surface produced using processes such as sanding, graving, embossing, or etching. The belt can be impermeable to air and water, or made permeable by processes such as punching, drilling, or laser drilling. Examples of structuring belts used in the NTT process can be viewed in International Publication Number WO 2009/067079 A1 and US Patent Application Publication No. 2010/0065234 A1.

After imprinting, the web is thermally pre-dried by moving hot air through the web while it is conveyed on the structured fabric. Thermal pre-drying can be used to dry the web to over 90% solids before it is transferred to a steam heated cylinder. The web is then transferred from the structured fabric to the steam heated cylinder though a very low intensity nip (up to 10 times less than a conventional press nip) between a solid pressure roll and the steam heated cylinder. The only portions of the web that are pressed between the pressure roll and steam cylinder rest on knuckles of the structured fabric, thereby, protecting most of the web from the light compaction that occurs in this nip. The steam cylinder and an optional air cap system, for impinging hot air, then dry the sheet to up to 99% solids during the drying stage before creping occurs. The creping step of the process again only affects the knuckle sections of the web that are in contact with the steam cylinder surface. Due to only the knuckles of the web being creped, along with the dominant surface topography being generated by the structured fabric, and the higher thickness of the TAD web, the creping process has much smaller effect on overall softness as compared to conventional dry crepe. After creping, the web is optionally calendered and reeled into a parent roll and ready for the converting process from a basesheet to a multi-ply material, if desired. Some TAD machines utilize fabrics (similar to dryer fabrics) to support the sheet from the crepe blade to the reel drum to aid in sheet stability and productivity. Examples of creped through air dried products are described in U.S. Pat. Nos. 3,994,771; 4,102,737; 4,529,480 and 5,510,002, hereby incorporated by reference.

A variation of the TAD process where the sheet is not creped, but rather dried to up to 99% using thermal drying and blown off the structured fabric (using air) to be optionally calendered and reeled also exits. This process is called UCTAD or un-creped through air drying process. An example of an uncreped through air dried product is described in U.S. Pat. No. 5,607,551, hereby incorporated by reference.

A newer process/method and paper machine system for producing tissue has been developed by the Voith GmbH and is being marketed under the name ATMOS. The process/method and paper machine system has several patented variations, but all involve the use of a structured fabric in conjunction with a belt press. The major steps of the ATMOS process and its variations are stock preparation, forming, imprinting, pressing (using a belt press), creping, calendering (optional), and reeling the web.

The stock preparation step is the same as a conventional or TAD machine would utilize. The purpose is to prepare the proper recipe of fibers, chemical polymers, and additives that are necessary for the grade of tissue being produced, and diluting this slurry to allow for proper web formation when deposited out of the machine headbox (single, double, or triple layered) to the forming surface. The forming process can utilize a twin wire former (as described in U.S. Pat. No. 7,744,726) a Crescent Former with a suction Forming Roll (as described in U.S. Pat. No. 6,821,391), or preferably a Crescent Former (as described in U.S. Pat. No. 7,387,706). The preferred former is provided a slurry from the headbox to a nip formed by a structured fabric (inner position/in contact with the forming roll) and forming fabric (outer position). The fibers from the slurry are predominately collected in the valleys (or pockets, pillows) of the structured fabric and the web is dewatered through the forming fabric. This method for forming the web results in a unique bulk structure and surface topography as described in U.S. Pat. No. 7,387,706 (FIG. 1 through FIG. 11). The fabrics separate after the forming roll with the web staying in contact with the structured fabric. At this stage, the web is already imprinted by the structured fabric, but utilization of a vacuum box on the inside of the structured fabric can facilitate further fiber penetration into the structured fabric and a deeper imprint.

The web is now transported on the structured fabric to a belt press. The belt press can have multiple configurations. A belt press configurations used in conjunction with a structured fabric can be viewed in U.S. Pat. No. 7,351,307, incorporated by reference herein, where the web is pressed against a dewatering fabric across a vacuum roll by an extended nip belt press. The press dewaters the web while protecting the areas of the sheet within the structured fabric valleys from compaction. Moisture is pressed out of the web, through the dewatering fabric, and into the vacuum roll. The press belt is permeable and allows for air to pass through the belt, web, and dewatering fabric, into the vacuum roll enhancing the moisture removal. Since both the belt and dewatering fabric are permeable, a hot air hood can be placed inside of the belt press to further enhance moisture removal as shown in FIG. 14 of U.S. Pat. No. 7,351,307. Alternately, the belt press can have a pressing device arranged within the belt which includes several press shoes, with individual actuators to control cross direction moisture profile, (see FIG. 28 in U.S. Pat. Nos. 7,951,269; 8,118,979, or FIG. 20 of U.S. Pat. No. 8,440,055, each of which are hereby incorporated by reference) or a press roll (see FIG. 29 in U.S. Pat. Nos. 7,951,269; 8,118,979, or FIG. 21 of U.S. Pat. No. 8,440,055, each of which are hereby incorporated by reference). The preferred arrangement of the belt press has the web pressed against a permeable dewatering fabric across a vacuum roll by a permeable extended nip belt press. Inside the belt press is a hot air hood that includes a steam shower to enhance moisture removal. The hot air hood apparatus over the belt press can made more energy efficient by reusing a portion of heated exhaust air from the Yankee air cap or recirculating a portion of the exhaust air from the hot air apparatus itself (see U.S. Pat. No. 8,196,314, hereby incorporated by reference). In further embodiments of the drying system composed of the hot air apparatus and steam shower in the belt press section are described in U.S. Pat. Nos. 8,402,673, 8,435,384 and 8,544,184 (each of which are hereby incorporated by reference).

After the belt press is a second press to nip the web between the structured fabric and dewatering felt by one hard and one soft roll. The press roll under the dewatering fabric can be supplied with vacuum to further assist water removal. This preferred belt press arrangement is described in U.S. Pat. Nos. 8,382,956, and 8,580,083, each of which are hereby incorporated by reference, with FIG. 1 showing the arrangement. Rather than sending the web through a second press after the belt press, the web can travel through a boost dryer (FIG. 15 of U.S. Pat. Nos. 7,387,706; 7,351, 307, each of which are hereby incorporated by reference), a high pressure through air dryer (FIG. 16 of U.S. Pat. Nos. 7,387,706; 7,351,307, each of which are hereby incorporated by reference), a two pass high pressure through air dryer (FIG. 17 of U.S. Pat. Nos. 7,387,706; 7,351,307, each of which are hereby incorporated by reference) or a vacuum box with hot air supply hood (FIG. 2 of U.S. Pat. No. 7,476,293, hereby incorporated by reference). In addition, U.S. Pat. Nos. 7,510,631, 7,686,923, 7,931,781 8,075,739, and 8,092,652 (each of which are hereby incorporated by reference) further describe methods and systems for using a belt press and structured fabric to make tissue products each having variations in fabric designs, nip pressures, dwell times, etc. and are mentioned here for reference. A wire turning roll can be also be utilized with vacuum before the sheet is transferred to a steam heated cylinder via a pressure roll nip (see FIG. 2a of U.S. Pat. No. 7,476,293, hereby incorporated by reference).

The sheet is now transferred to a steam heated cylinder via a press element. The press element can be a through drilled (bored) pressure roll (FIG. 8 of U.S. Pat. No. 8,303,773, hereby incorporated by reference), a through drilled (bored) and blind drilled (blind bored) pressure roll (FIG. 9 of U.S. Pat. No. 8,303,773, hereby incorporated by reference), or a shoe press (see U.S. Pat. No. 7,905,989, hereby incorporated by reference). After the web leaves this press element to the steam heated cylinder, the % solids are in the range of 40-50% solids. The steam heated cylinder is coated with chemistry to aid in sticking the sheet to the cylinder at the press element nip and also aid in removal of the sheet at the doctor blade. The sheet is dried to up to 99% solids by the steam heated cylinder and installed hot air impingement hood over the cylinder. This drying process, the coating of the cylinder with chemistry, and the removal of the web with doctoring is explained in U.S. Pat. Nos. 7,582,187 and 7,905,989, each of which are hereby incorporated by reference. The doctoring of the sheet off the Yankee, creping, is similar to that of TAD with only the knuckle sections of the web being creped. Thus the dominant surface topography is generated by the structured fabric, with the creping process having a much smaller effect on overall softness as compared to conventional dry crepe.

The web is now optionally calendered, slit, and reeled in preparation for the converting process.

The ATMOS manufacturing technique is often described as a hybrid technology because it utilizes a structured fabric like the TAD process, but also utilizes energy efficient means to dewater the sheet like the Conventional Dry Crepe process. Other manufacturing techniques which employ the use of a structured fabric along with an energy efficient dewatering process are the ETAD process and NTT process. The ETAD process and products are described in U.S. Pat. Nos. 7,339,378, 7,442,278, and 7,494,563, each of which are hereby incorporated by reference. This process can utilize any type of former such as a Twin Wire Former or Crescent Former. After formation and initial drainage in the forming section, the web is transferred to a press fabric where it is conveyed across a suction vacuum roll for water removal, increasing web solids up to 25%. Then the web travels into a nip formed by a shoe press and backing/transfer roll for further water removal, increasing web solids up to 50%. At this nip, the web is transferred onto the transfer roll and then onto a structured fabric via a nip formed by the transfer roll and a creping roll. At this transfer point, speed differential can be utilized to facilitate fiber penetration into the structured fabric and build web caliper. The web then travels across a molding box to further enhance fiber penetration if needed. The web is then transferred to a Yankee dryer where is can be optionally dried with a hot air impingement hood, creped, calendared, and reeled. The NTT process and products are described in International Patent Application Publication No. WO 2009/061079 A1, hereby incorporated by reference. The process has several embodiments, but the key step is the pressing of the web in a nip formed between a structured fabric and press felt. The web contacting surface of the structured fabric is a non-woven material with a three dimensional structured surface comprised of elevation and depressions of a predetermined size and depth. As the web is passed through this nip, the web is formed into the depression of the structured fabric since the press fabric is flexible and will reach down into all of the depressions during the pressing process. When the felt reaches the bottom of the depression, hydraulic force is built up which forces water from the web and into the press felt. To limit compaction of the web, the press rolls will have a long nip width which can be accomplished if one of the rolls is a shoe press. After pressing, the web travels with the structured fabric to a nip with the Yankee dryer, where the sheet is optionally dried with a hot air impingement hood, creped, calendered, and reeled.

In embodiments, the fabric in the inner position of a former, such as the Crescent former, is a structured fabric. Structured fabrics can be manufactured using 3D printing techniques and materials that can be utilized with 3D printers. The structured fabric may comprise a cast or extruded polymer film with holes produced using a laser. The structured fabric may be a woven structure that utilizes monofilaments (yarns, threads) made of synthetic polymers (usually polyethylene, polypropylene, or nylon) that may be overlaid with a patterned polymer resin. The structured fabric may be produced using any of various processes for making a three-dimensional object primarily through additive processes in which successive layers of material are laid down under computer control. These processes are generally classified as 3-D printing technologies and include but are not limited to any of the following: Fused Deposition Modeling (FDM), PolyJet Technology, Selective Laser Melting (SLM), Direct Metal Laser Sintering (DMLS), Selective Laser Sintering (SLS), Stereolithography (SLA), or Laminated Object Manufacturing (LOM).

In Conventional Dry Crepe and Conventional Wet Crepe methods, a nascent web is formed in a forming structure, the web is transferred to a dewatering felt where it is pressed to remove moisture, and the web is then adhered to a Yankee Dryer. The web is then dried and creped from the Yankee Dryer and reeled. When creped at a solids content of less than 90%, the process is referred to as Conventional Wet Crepe. When creped at a solids content of greater than 90%, the process is referred to as Conventional Dry Crepe.

Additional processes for manufacturing wetlaid tissue can be found in U.S. Pat. No. 8,968,517 and U.S. patent application Ser. No. 14/561,802.

Single Ply Product

Figure 2:
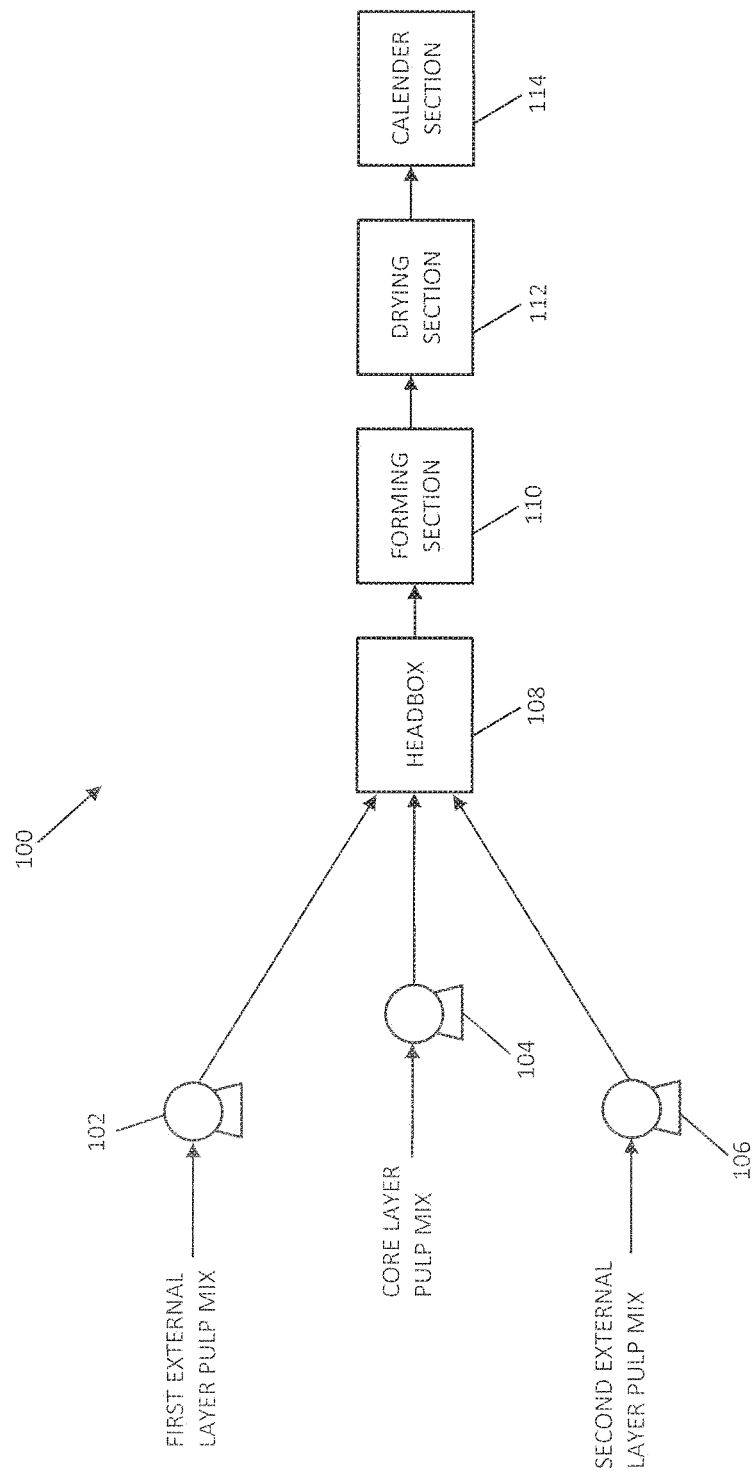
FIG. 2 is a block diagram of a system for manufacturing a single ply of a wipe according to an exemplary embodiment of the present invention.

FIG. 2 is a block diagram of a system for manufacturing a single ply of a wipe, generally designated by reference number 100, according to an exemplary embodiment of the present invention. The system 100 includes a first exterior layer fan pump 102, a core layer fan pump 104, a second exterior layer fan pump 106, a headbox 108, a forming section 110, a drying section 112 and a calendar section 114. The headbox 108 is a stratified headbox (e.g., a triple layer headbox for a three layer ply, a double layer headbox for a two layer ply) to form multilayer plies. Alternatively, multiple headboxes may be provided, with a separate headbox corresponding to a separate layer of the multi-layer wipe. In embodiments, all three headbox layers may be formed using foam forming. In other embodiments, only the core layer or no layers are formed using foam forming. In another exemplary embodiment of the invention, long fibers may be incorporated via a regular water forming headbox separate from headbox 108.

The first and second exterior layer fan pumps 102, 106 deliver the furnish of the first and second external layers 2, 4 to the headbox 108, and the core layer fan pump 104 delivers the foamed furnish of the core layer 3 to the headbox 108. The foamed furnish includes a dispersion of fibers in a foamed liquid containing water and a surfactant. The foam forming surfactants could be anionic, cationic, non-ionic or amphoteric depending on their ability to generate a foamed dispersion. Some examples of anionic surfactants include sodium dodecyl sulfate (SDS), sodium alkyl ether sulphate (SAES) and alkyl ketene dimer (AKD) based labile surfactant. A typical example of ionic surfactants is alpha olefin sulfonate and some examples of non-ionic surfactants include alkyl glucosides and ethoxylated alcohols such as a peg-6 lauramide. The following steps are performed:

Deposition of Slurry from Headbox onto Forming Surface: As is known in the art, the headbox delivers a wet web of pulp onto a forming wire, such as a Fourdrinier wire or a twin wire former, within the forming section 110. The wet web is delivered to the forming wire with the core layer 3 disposed between the first and second external layers 2, 4. The laying down of the core layer 3 results in a formed fibrous web disposed between the first and second external layers 2, 4. If any layer is foam formed, this may be accomplished in a single layer or multilayer headbox using surfactants injected into the thin stock loop and modified pumping systems specifically designed to handle entrained air.

Drainage of Slurry across Forming Surface to Dewater the Nascent Web: At least some dewatering may occur in the forming section 110. Water and surfactant removed from any foam formed layer during dewatering may be recycled.

Imprinting the Web Using a Structured Fabric: After formation in the forming section 110, the wet web may be imprinted with a structured fabric.

Drying the Web: Next, the web is transferred to the drying section 112. Within the drying section 112, the wet web may be dewatered using an ATMOS system, such as a twin wire ATMOS system as described in U.S. Pat. No. 7,744,726, the disclosure of which is incorporated herein by reference in its entirety, or an NTT system, available from Valmet Corporation, of Espoo Finland, or through TAD technology. After dewatering, the dewatered web may be dried further using a Yankee drying cylinder/drum with or without a hot air hood installed over the Yankee drying cylinder.

As noted in regards to an ATMOS drying process, the web is pressed against a dewatering fabric across a vacuum roll by an extended nip belt press. The vacuum roll applies negative pressure to a surface of the permeable dewatering fabric which is opposite to a surface of the permeable dewatering fabric which contacts the web, drawing moisture from the web through the dewatering fabric into the vacuum roll. The vacuum roll may have a diameter of between approximately 1000 mm and approximately 2500 mm. In addition, in embodiments, the permeable dewatering fabric comprises a felt with a batt layer. The fabric may have a caliper of between approximately 0.1 mm and approximately 15 mm, a permeability value of between approximately 1 cfm and approximately 500 cfm, an overall density of between approximately 0.2 $g/cm^3$ and approximately 1.1 $g/cm^3$ and a weight of between approximately 350 $g/m^2$ and approximately 3000 $g/m^2$. Also, in embodiments, an extended nip belt press comprises a permeable belt with a tension of between approximately 20 kN/m and approximately 100 kN/m, a permeability value of between approximately 100 cfm and approximately 1200 cfm, a surface contact area of the paper web side that is between approximately 0.5% and approximately 90% when not under tension, and an open area of between approximately 1.0% and approximately 85%. In embodiments, the extended nip of the belt press has an angle of wrap of between approximately 30 degrees and approximately 180 degrees, and, in embodiments, the extended nip has a nip length of between approximately 800 mm and approximately 2500 mm.

A hot air impingement hood may be installed inside of the belt press, and a steam shower may be installed inside the hot air impingement hood. Where the hood is used, a portion of exhaust air from an air cap installed over the steam heated cylinder is utilized as makeup air for the installed hood inside the belt press. Additionally, shoe presses may be installed inside the hot air impingement hood or may be installed inside of the belt press rather than a hot air impingement hood. Alternatively, a press roll may be installed inside of the belt press rather than installing shoe presses or a hot air impingement hood.

In an exemplary embodiment, a creping adhesive is applied to the drum prior to the dewatered web contacting the drum. After drying, a creping blade is used to remove the wipe from the Yankee drying drum, such as with a steel or ceramic doctor blade. The creping may be performed with or without a hot air impingement hood. At that point, the web has a solids content of approximately 15% to 1% solids.

Optionally Calendering the Web: The wipe may then be calendered in a subsequent stage within the calender section 114. According to an exemplary embodiment, calendering may be accomplished using a number of calender rolls (not shown) that deliver a calendering pressure in the range of 0-100 pounds per linear inch (PLI). In general, increased calendering pressure is associated with reduced caliper and a smoother tissue surface.

Reeling the Web onto a Parent Roll and Unwinding the Web: The formed web may be reeled on a parent roll, such as one of the parent rolls 208, 209 shown in FIG. 3. For a single ply wipe, the parent roll is unwound while a binder is applied to the roll.

To meet the "flushability" requirements of IVDA and to reduce the events of pluggage within household sanitation systems as well as wastewater treatment facilities, nonwoven wipes can incorporate unique binders. The binders allow the wipe to be pre-moistened and retain its strength, but the binder will dissociate causing the nonwoven to lose its strength and disperse when flushed into a toilet. The binder may be used as an adhesive or as part of the adhesive to hold the multiple plies together before the wipe is disposed of.

Some examples of these binders are polymers that are insoluble in warm water, but are soluble in cold water, such as found in a toilet. An example of a nonwoven product incorporating this type of binder is shown in U.S. Pat. No. 5,509,913. Other types of binders are polymers that are ion sensitive. When a wipe is pre-moistened with a solution containing a high ion concentration, the binder remains insolvent and the nonwoven retains its strength. When flushed into a toilet t containing soft water, the binder dissociates and the wipe can disperse. Other types of binders suitable for wipes that may be "flushable" by INDA standards are known, such as binders described in U.S. Pat. Nos. 5,281,306 and 7,157,389.

The binder may be applied via roll coating such as with a roto-gravure or flexographic coating that is applied to the web. As another alternative, the application of the binder may be performed via spray coating or spin disc coating equipment. The binder may be applied in a particular pattern with surface coverage of the web ranging from 0 to 100%, and more preferably 50% surface coverage, or most preferably 10 to 30% surface coverage. The pattern may be a repeating pattern with each component of the pattern defining an open area free of binder. Exemplary patterns include polygonal-shaped patterns, such as diamond or triangular shaped patterns.

When pre-moistening the wipe, the binder contributes to retaining the integrity of the wipe prior to disposal. The particular binder that is used may be, for example, a polyethylene, vinyl acetate ethylene copolymers, vinyl-based or acrylic binders, or combinations thereof. Thus, possible binders may include a poly(vinyl) alcohol, poly(vinyl) acetate, poly (ethylene) (vinyl) alcohols, poly (ethylene) (vinyl) acetate, copolymers of vinyl acetate-ethylene, starch based chemistries or combinations thereof. The binder may also contain additional components such as a cross-linking agent including epoxy, amide and anhydride based chemistries, or ion sensitive polymers comprising acrylic acid, alkyl or aryl acrylates, terpolymers which comprise partially neutralized acrylic acid, butyl acrylate and 2-ethylhexyl acrylate. The binder also may comprise additional trigger chemistries ranging from 0.1 to 10% by weight such as mono or divalent salt selected from NaCl, NaBr, KCl, $NH_4Cl$, $Na_2SO_4$, $AnCl_2$, $CaCl_2$, $MgCl_2$, $MgSO_4$, $NaNO_3$, $NaSO_4CH_3$, $BNa_3O_3$, $NaB_4O_7$ or combinations thereof. The trigger chemistries, such as boric acid, can alternatively or also be included in the cleansing solution that is applied to the wipe 1.

After being applied, the binder may be cured at high temperatures in the range of 200 to 250° F. using methods such as infrared, UV, or other non-contact heating devices.

After application and curing of the binder, the single ply wipe may be cut or perforated, folded (e.g., Z-fold), stacked and packaged with wetting/cleansing solution. The cleaning solution is preferably applied to the stack of dry wipes inside the package before the package is sealed. Alternately, the wetting solution can be applied to the inside of the package and the stack of dry wipes placed on top of the solution inside the package. The cleansing or wetting/cleaning solution may contain a trigger chemistry ranging from 0.1 to 10% by weight such as mono or divalent salt selected from NaCl, NaBr, KCl, $NH_4Cl$, $Na_2SO_4$, $AnCl_2$, $CaCl_2$, $MgCl_2$, $MgSO_4$, $NaNO_3$, $NaSO_4CH_3$, $BNa_3O_3$, $NaB_4O_7$ or combinations thereof. A cleansing solution may include glycol based cross-linking chemistry, anhydrides and epoxy groups, cyclo-dextrins adapted to release fragrances, and/or at least one of aloe or shea butter. The cleansing solution may be present in the amount of 40% to 80% by weight. A cleansing solution may include purified water and a combination of one or more of the following: humectants, preservatives, moisturizers, surfactants, chelating agents, pH buffer and aromatic compounds. The packaging may be a soft package comprised of polymer with a re-sealable opening or a hard polymer tub with a low coefficient of friction opening covered with a hinged lid. Either packaging option can contain a zinc strip located inside the packaging for additional biological growth control. Either packaging option can contain adhesive strips or suction cups for mounting.

Multi-Ply Product

In another exemplary embodiment, a wipe according to the present invention may comprise two or more plies formed from two webs formed according to the process described with respect to FIG. 2 that are laminated together to create a multi-ply wipe. Each ply of a multi-ply wipe of the present invention may be made of the same type(s) of fibers or different fibers may be used in some or all of the plies. In a preferred embodiment, the plies have the same multi-layer tissue structure and composition.

Where the wipe is to be formed of two plies, the wipes are obtained by applying a binder between the two or more plies, embossing the plies, and then using a marrying roll following the embossment.

Figure 3:
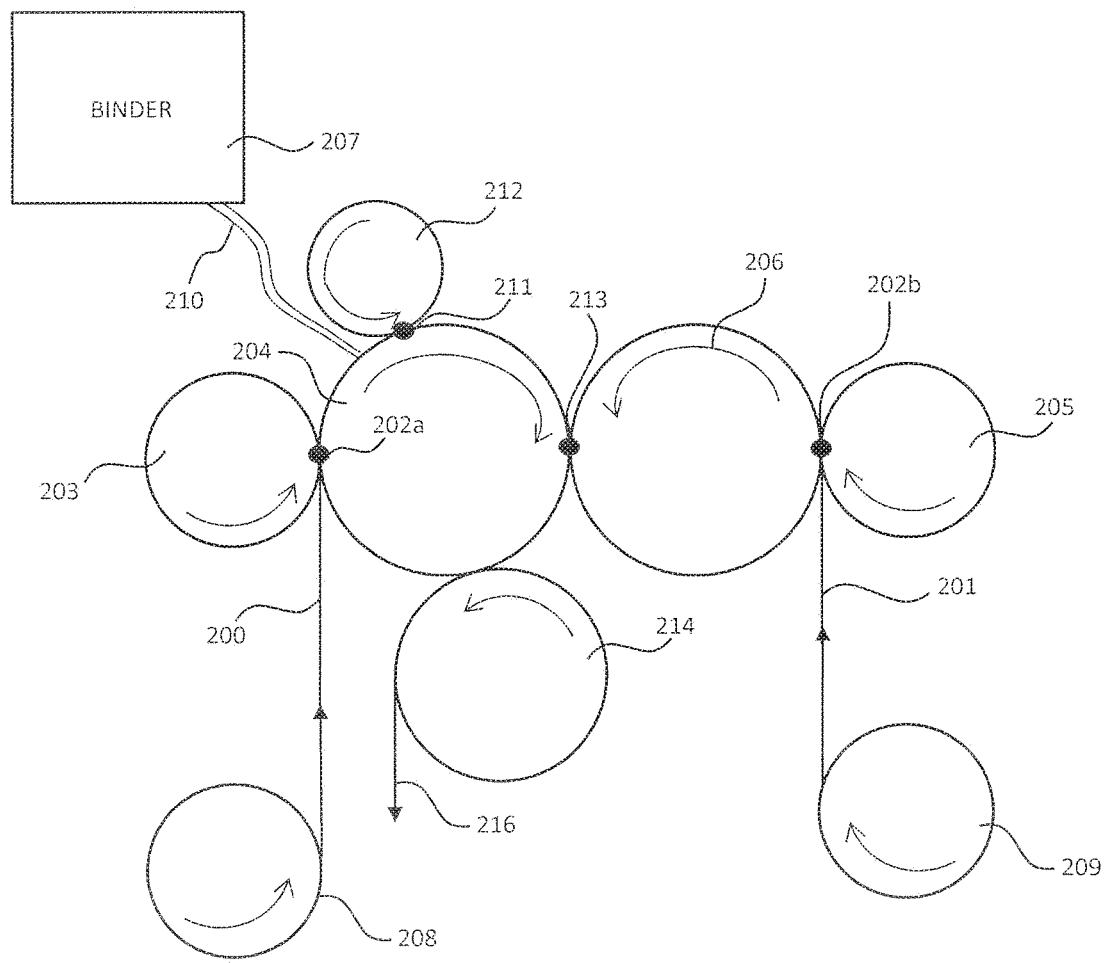
FIG. 3 is a block diagram of a system for manufacturing a multi-ply wipe product according to an exemplary embodiment of the present invention.
Figure 4:
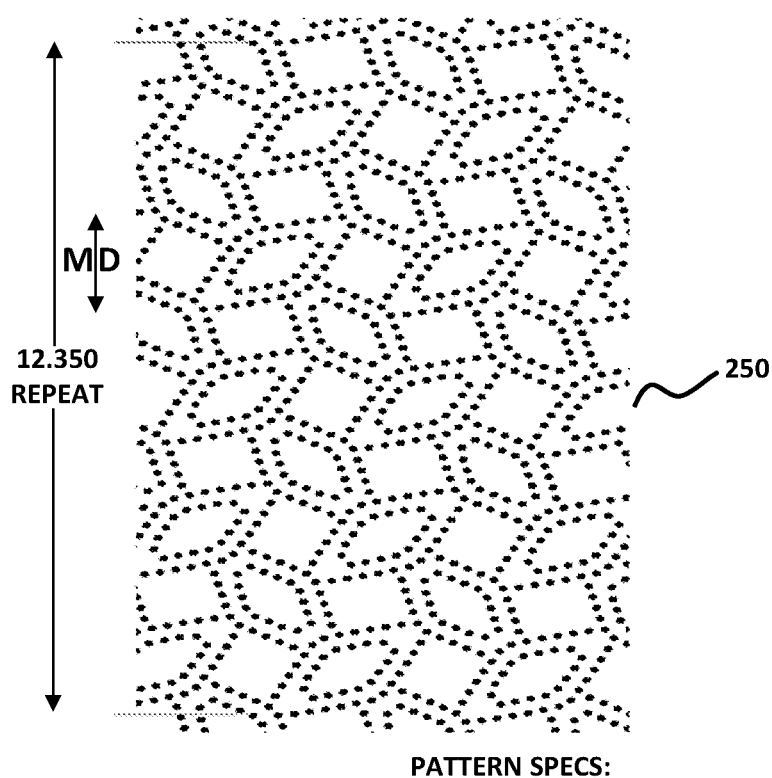
FIG. 4 shows an embodiment of a wipe that has an embossment pattern in accordance with an exemplary embodiment of the present invention.

FIG. 3 shows an apparatus for manufacturing a laminate of two plies of a wipe that are joined to each other, in a face-to-face relationship, using an exemplary embodiment of the present invention. As shown in the figure, each of two webs 200, 201 of single ply web, which may be manufactured, for example, according to a method described above, is unwound and fed from each of parent rolls 208, 209 to respective pairs of mated pressure rolls 203, 205 and substantially axially parallel embossing rolls 204, 206. A first web 200 is thus fed through a nip 202a formed by pressure roll 203 and embossing roll 204 (also known as a pattern roll) and a second web 201 is likewise fed through a nip 202b between pressure roll 205 and embossing roll 206. The embossing rolls 204, 206, which rotate in the illustrated directions, impress an embossment pattern onto the webs as they pass through nip 202a and 202b. An exemplary embossment pattern for the wipe is shown in FIG. 4. After being embossed, each ply may have a plurality of embossments protruding outwardly from the plane of the ply towards the adjacent ply. The adjacent ply likewise may have opposing protuberances protruding towards the first ply. If a three ply product is produced by adding a third pair of mated pressure and embossing rolls, the central ply may have embossments extending outwardly in both directions.

To perform the embossments at nips 202a and 202b, the embossing rolls 204, 206, which may be hard or soft covered, have embossing tips or embossing knobs that extend radially outward from the rolls to make the embossments. In embodiments, the depth of the knobs may be between 25 to 1000 thousandths of an inch. In the illustrated embodiment, embossing is performed by nested embossing in which the crests of the embossing knobs on one embossing roll intermesh with the embossing knobs on the opposing embossing roll and a nip is formed between the embossing rolls. As the web is fed through nips 202a and 202b, a pattern is produced on the surface of the web by the interconnectivity of the knobs on an embossing roll with the open spaces of the respective pressure roll.

An adhesive applicator roll 212 is positioned upstream of the nip 213 formed between the two embossing rolls and is aligned in an axially parallel arrangement with one of the two embossing rolls to form a nip therewith. A binder is fed from a tank 207 via a conduit 210 to applicator roll 212. The applicator roll 212 transfers a binder to an interior side of embossed ply 200 to adhere the at least two plies 200, 201 together, wherein the interior side is the side of ply 200 that comes into a face-to-face relationship with ply 201 for lamination. The binder is applied to the ply at the crests of the embossing knobs 205 on embossing roll 204. The binder may alternatively or in addition applied via roll coating such as with a roto-gravure or flexographic coating that is applied to the one or two webs (or more webs, when present) before the webs are pressed together between the embossing rolls 204 or 206 to be plied. As another alternative to the use of an applicator roll 212 to apply the binder or in addition to that, the application of the binder may be performed via spray coating or spin disc coating equipment to the one or two webs before the webs are pressed together between the two embossing rolls. As described previously in regards to the single ply wipe, the binder may be applied in a particular pattern with surface coverage of the web ranging from 0 to 100%, and more preferably 50% surface coverage.

After being applied, the binder may be cured at high temperatures in the range of 200 to 250° F. using methods such as infrared, UV, or other non-contact heating devices.

The webs are then fed through the nip 213 where the embossing patterns on each embossing roll 204, 206 mesh with one another. After application of the embossments and the binder, a marrying roll 214 is used to apply pressure for lamination. The marrying roll 214 forms a nip with the same embossing roll 204 that forms the nip with the applicator roll 212, downstream of the nip formed between the two embossing rolls 204, 206. The marrying roll 214 is generally needed because, in nested embossing, the crests of the nested embossing knobs 205 typically do not touch the perimeter of the opposing roll 206 at the nip 213 formed therebetween.

The specific pattern that is embossed on the absorbent products can improve the adhesion properties of the plies. In an exemplary embodiment, the embossed area (or "bond area") on any ply may cover between approximately 5 to 15% of the surface area of the ply. The size of each embossment may be between approximately 0.04 to 0.08 square centimeters. The depth of each embossment may be between 0.28 and 0.43 centimeters (0.110 and 0.170 inches) in depth.

FIG. 4 shows a sample pattern embossed on a wipe 250 according to an embodiment of the present invention. In the illustrated pattern, the embossed area covers approximately 13% of the surface, the embossment depth is approximately 0.34 centimeters (0.135 inches), and the embossment diameter is approximately 0.92 centimeters (0.115 inches).

The laminate is then cut or perforated, folded (e.g., Z-fold), stacked and packaged with wetting/cleansing solution. The cleaning solution is preferably applied to the stack of dry wipes inside the package before the package is sealed. Alternately, the wetting solution can be applied to the inside of the package and the stack of dry wipes placed on top of the solution inside the package. The cleansing or wetting/cleaning solution may contain a trigger chemistry ranging from 0.1 to 10% by weight such as mono or divalent salt selected from NaCl, NaBr, KCl, NH$_4$Cl, Na$_2$SO$_4$, AnCl$_2$, CaCl$_2$, MgCl$_2$, MgSO$_4$, NaNO$_3$, NaSO$_4$CH$_3$, BNa$_3$O$_3$, NaB$_4$O$_7$ or combinations thereof. A cleansing solution may include glycol based cross-linking chemistry, anhydrides and epoxy groups, cyclo-dextrins adapted to release fragrances, and/or at least one of aloe or shea butter. The cleansing solution may be present in the amount of 40% to 80% by weight. A cleansing solution may include purified water and a combination of one or more of the following: humectants, preservatives, moisturizers, surfactants, chelating agents, pH buffer and aromatic compounds. The packaging may be a soft package comprised of polymer with a re-sealable opening or a hard polymer tub with a low coefficient of friction opening covered with a hinged lid. Either packaging option can contain a zinc strip located inside the packaging for additional biological growth control. Either packaging option can contain adhesive strips or suction cups for mounting.

In some exemplary embodiments, the following properties are exhibited by flushable and dispersible multi-ply wet wipes made using a TAD process:

(1) MD Tensile Strength: Between 30 N/m to 250 N/m, preferably between 50 N/m to 150 N/m;

(2) CD Tensile Strength: Between 30 N/m to 250 N/m, preferably between 50 N/m to 150 N/m;

(3) Wet Burst Strength: Between 1000 gf to 10000 gf preferably between 2000 gf to 5000 gf;

(4) Caliper: Between 300 to 1500 microns, preferably between 400 to 1250 microns.

In some exemplary embodiments, the following properties may be exhibited by single ply wipes and multi-ply flushable and dispersible wet wipes made using a UCTAD process:

(1) MD Tensile Strength: Between 30 N/m to 250 N/m, preferably between 50 N/m to 150 N/m;

(2) CD Tensile Strength: Between 30 N/m to 250 N/m, preferably between 50 N/m to 150 N/m;

(3) Wet Burst Strength: Between 1000 gf to 10000 gf preferably between 2000 gf to 5000 gf;

(4) Caliper: Between 300 to 1500 microns, preferably between 400 to 1250 microns.

The following discussion describes the techniques that were used to determine values for basis weights, fiber length, MD and CD stretch and tensile strength, and caliper, in connection with the various exemplary embodiments of the present invention.

Basis Weight

The basis weight was measured in grams/m$^2$ using the following process: Using a dye and press, six approximately 76.2 mm by 76.2 mm (approximately 3 inch×3 inch) square samples were cut from each two-ply product that was tested with care being taken to avoid any web perforations in the sample. The samples were placed in an oven at 105 degrees Celsius for 5 minutes and were thereafter weighed on an analytical balance to the fourth decimal point. The weight of the sample in grams was then divided by (0.0762 m)$^2$ to determine the basis weight in grams/m$^2$.

Fiber Length Measurements Using Fqa

The length weighted mean fiber length measurements were taken using the Fiber Quality Analyzer (Product Code LDA02) purchased from OpTest Equipment (900 Tupper, Hawkesbury, Ontario, Canada K6A 3S3). Installation, connections, startup procedure, initial system check, and performance checks were completed using the LDA02 FQA Operation Manual.

The instrument operating principles are as follows:

The instrument uses an optics box composed of a flow cell, light source, circular polarizing filters, and a CCD Camera to measure the length, width, coarseness, kink, and curl of fiber in a dilute slurry that passes through the optics box. Diluted fibers immersed in clean water enter the center port at the bottom of the flow cell. The fibers entering the center port pass through a thin planar channel. This channel helps to gently orient the fiber two-dimensionally so that the fiber is fully viewed by the camera. High quality water enters the two side ports at the bottom of the flow cells which sandwich the thin plane containing the fiber. This helps to orient the fiber and protect the flowcell from contaminants. The far-red spectrum light source is located on the left hand side of the flow cell. The far-red spectrum light passes through a circular polarizing filter. The polarized light then passes through the window of the flow cell. If the polarized light strikes a fiber, a phase shift will occur which will allow the light to pass through the second circular polarizing filter and reach the camera located on the right hand side of the flow cell. Only higher organized crystalline structure are able to cause a phase shift in circular polarized light. Therefore, the instrument will not detect kinks, pitch, or scale which would affect results. The CCD Camera pixels are zero cross talk, zero defect, with 256 greylevels, and a pixel resolution of 7 micrometers for width and 14 micrometers for length. The software on the instrument uses the images from the camera to then perform the aforementioned measurements of the fibers.

In order to prepare a representative sample of dilute fibers from a wipe, the sample was socked in clean water for at least 4 hours. Fiber clusters were gently pulled from the soaked wipe and TAPPI T 205 procedure was followed to disperse the fiber clusters using a disintegrator. The samples were not cut from the sheet to avoid shortening of the fibers. The preferred consistency of the dilute fiber slurry was no more than 2 mg/L before running the sample through the Fiber Quality Analyzer.

Once measurement of the prepared sample was ready, the "Sample Identification" procedure was followed in the LDA02 FQA Operation Manual before measuring the sample to properly identify and save the fiber length data in the instrument for later retrieval. Next, the "Test Procedure" steps were followed in the LDA02 FQA Operation Manual (place the sample in the beaker holder, under "Predefined Settings" select TAPPI T271 and then select "Start"). At this stage, the instrument pulled the dilute fiber slurry from the beaker and performed the measurements that includes length weighted mean fiber length. Once the beaker was empty, "Results" was selected to see these measurements and record the length weighted mean fiber length.

Fiber Length Measurement Using Microscope

The fiber length measurement using a microscope was performed using the following equipment:

Microscope: VHX-700F Digital Microscope Multi Scan by Keyence

Software: 2009-2011 KEYENCE CORPORATION, Version 1.3.0.7, System Version 1.21

The following procedure was followed:
1) Dry wet wipe in oven to evaporate wetting solution at 105° C. for 5 minutes.
2) Wearing Nitrile gloves pull 3 quarter-sized samples from the wet wipe.
3) Submerge the samples in 35 mL of water in a 50 mL plastic vial.
4) Cap the vial and allow the sample to be continually inverted for a 24 hour period using a Stuart Rotator SB3 device.
5) Once the samples have been successfully washed and fibers appear separated, pipette 4-5 drops of the mixture onto a glass slide and allow the slide to dry.
6) Create 5 slides per sample.
7) Once dry, place the glass slide under the Keyence VHX-700F microscope.
8) Locate the longest 3 visible fibers on each slide.
9) On each of the three fibers, using the VHX-700F software, click on Measure/Text
10) Then click on Measure/Comment.
11) Under the Main tab, click on the Multi-pt. measurement tool.
12) Trace the long fiber using the Multi-pt. tool and record the length.
13) Record the length of the longest fiber measured of each sample.

Stretch & Md, Cd, and Wet Cd Tensile Strength Testing

An Instron 3343 tensile tester, manufactured by Instron of Norwood, Mass., with a 100N load cell and 25.4 mm rubber coated jaw faces was used for tensile strength measurement. Prior to measurement, the Instron 3343 tensile tester was calibrated. After calibration, 8 strips of 2-ply product, each 2.54 cm by 10.16 cm (one inch by four inches), were provided as samples for each test. When testing MD (Material Direction) tensile strength, the strips are cut in the MD direction. When testing CD (Cross Direction) tensile strength, the strips are cut in the CD direction. One of the sample strips was placed in between the upper jaw faces and clamp, and then between the lower jaw faces and clamp with a gap of 5.08 cm (2 inches) between the clamps. A test was run on the sample strip to obtain tensile and stretch. The test procedure was repeated until all the samples were tested. The values obtained for the eight sample strips were averaged to determine the tensile strength of the tissue. When testing CD wet tensile strength, the strips were placed in an oven at 105 degrees Celsius for 5 minutes and saturated with 75 microliters of deionized water immediately prior to pulling the sample.

Caliper Testing

A Thwing-Albert ProGage 100 Thickness Tester, manufactured by Thwing Albert of West Berlin, N.J. was used for the caliper test. Eight 100 mm×100 mm square samples were cut from a 2-ply product. The samples were then tested individually and the results were averaged to obtain a caliper result for the base sheet.

Wet Burst Procedure

The following procedure was followed using a Twing Albert tensile tester EJA series part #1750-2011with a 250N load cell and wet burst attachment part #SMT1-25N-354 manufactured by Twing-Albert Instrument Company (14 W Collings Ave, West Berlin, N.J. 08091):
1. Place sample on the lower grip.
2. Press "Upper Grip" on the control panel, located on the side of the apparatus to close the clamps.
3. Use the "Down" Button on the control panel to lower the top arm until it is within 1-2 inches of the sample.
4. Press the green test button on the same control panel, or in the upper left corner of the computer program, to begin the test.
5. When the test is complete, release the clamps using the same "Upper Grip" button and remove the sample.
6. Test eight samples and record the average maximum force.

The following Examples illustrate the various features and advantages of the present invention.

Example 1

A flat pack of 2-ply pre-moistened wipes (30% solids) with dimensions of 5.25 inches by 7 inches were manufactured using the wet-laid TAD process and laminated using the deco emboss method with an 80% vinyl acetate-ethylene copolymer, 20% PVOH binder. The resulting 2-ply product had the following product attributes: Basis Weight 81.89 g/m$^2$, Caliper 0.453 mm, MD tensile of 55.5 N/m, CD tensile of 59.9 N/m, and a burst strength of 1848 gf.

The wipe web was formed on a wet laid TAD asset with a twin wire solid C-wrap former with a 3 layer headbox. The furnish to each outer layer was composed of 50% El Dorado *Eucalyptus* pulp, 40% Grand Prairie NB SK, and 10% 6 mm Lyocell. The NB SK and Lyocell were co-refined in a conical refiner imparting 80 kwh/ton. The center layer was composed of 80% Grand Prairie NBSK and 20% 6 mm Lyocell fiber co-refined in a conical refiner imparting 80 kwh/ton. Three kg/ton of a copolymer of glyoxal (DPD-589 from Solenis, 500 Hercules Road, Wilmington Del., 19808) was added to the co-refined NBSK and Lyocell at the discharge of the refiner. The fiber and chemicals mixtures were diluted to a solids of 0.5% consistency and fed to separate fan pumps which delivered the slurry to the triple layered headbox. The headbox pH was controlled to 7.0 by addition of a caustic to the thick stock before the fan pumps. The headbox deposited the slurry to a nip formed by a forming roll, an outer forming wire, and an inner fabric. The slurry was drained through the outer wire, which was a KT194-P design from Asten Johnson of Charleston, S.C., and transferred to a plain weave inner wire. The web was then transferred to a structured TAD fabric with a 10 shed weave, 0.35 mm warp and 0.50 mm shute monofilament, at 15% wire crepe. A single slotted vacuum box of 18 mm with 35 kPa of vacuum was used to facilitate transfer to the structured fabric upon which the web traveled over a four slotted molding box (each slot at 19 mm), with 80 kPa of vacuum. The web was dried using two through air drier drums to 90% solids before being transferred to a steam heated Yankee dryer cylinder. The Yankee dryer had 18 mg/m$^2$ of a PAE based adhesive applied as well as 45 mg/m$^2$ of a polyvinyl alcohol and 3 mg/m$^2$ of a release oil applied using a double overlap spraybar. The sheet was creped from the Yankee dryer using a 45 degree ceramic blade at 98% solids and reeled into parent rolls.

Two wipe parent roll webs were laminated together using embossing in the deco configuration (only the top sheet is embossed with binder applied to the inside of the top sheet at the high points derived from the embossments using a binder supplied by an applicator roll) with the second exterior layer of each web facing each other. The top sheet emboss roll was a patterned roll with embossments leading to 40% contact with the applicator roll. The binder used 80% copolymer of vinyl acetate-ethylene dispersion purchased from Wacker of Munchen, Germany under the product name of VINNAPAS® 400, and 20% polyvinyl alcohol purchased from Sekisui (1501 LBJ Freeway, Suite 530 Dallas Tex. 75234) under the tradename Selvol™ 523. The binder was diluted to 25% solids. The laminated wipes were then cut to size and packaged in a wetting solution to a solids concentration of 30%. The wetting solution was 95% purified water, 4.4% boric acid with the remainder a mixture of humectants, preservatives, moisturizers, surfactants, chelating agents, pH buffer, and aromatic compounds.

Example 2

A flat pack of 2-ply pre-moistened wipes (30% solids) with dimensions of 5.25 inches by 7 inches were manufactured using the wet-laid TAD process and laminated using the deco emboss method with an 80% vinyl acetate-ethylene copolymer, 20% polyvinyl alcohol binder. The resulting 2-ply product had the following product attributes: Basis Weight 74 g/m$^2$, Caliper 0.939 mm, MD tensile of 75.6 N/m, CD tensile of 70.1 N/m, and a burst strength of 2404 gf.

The wipe web was formed on a wet laid TAD asset with a twin wire solid C-wrap former with a 3 layer headbox. The furnish to all layers was 80% Grand Prairie NBSK and 20% 6 mm Lyocell. This NBSK and Lyocell were co-refined in a conical refiner imparting 140 kwhr/ton. Four kg/ton of glyoxalated polyacrylamide (Hercobond 1194 from Solenis of Wilmington, Del.) was added to the corefined NBSK and Lyocell at the discharge of the refiner. 3 kg/ton of OmyaSoft 140 ground calcium carbonate from Omya Inc (9987 Carver Road Suite 300 Cincinnati Ohio 45242) was added to the suction of the refiner. 10 kg/ton of Redibond® 2038 amphoteric starch from Ingredion (5 Westbrook Corporate Center Westchester, Ill. 60154) and 2 kg/ton of Hercobond™ 6350 polyvinyl amine from Solenis was added to the suction of each of the three layer fan pumps. The fiber and chemicals mixtures were diluted to a solids of 0.5% consistency and fed to separate fan pumps which delivered the slurry to the triple layered headbox. The headbox pH was controlled to 7.0 by addition of a caustic to the thick stock before the fan pumps. The headbox deposited the slurry to a nip formed by a forming roll, an outer forming wire, and an inner fabric. The slurry was drained through the outer wire, which was a KT194-P design from Asten Johnson of Charleston, S.C., and transferred to a plain weave inner wire. The web was then transferred to a structured TAD fabric with a 10 shed weave, 0.35 mm warp and 0.50 mm shute monofilament, at 15% wire crepe. A single slotted vacuum box of 18 mm with 35 kPa of vacuum was used to facilitate transfer to the structured fabric upon which the web traveled over a four slotted molding box (each slot at 19 mm), with 80 kPa of vacuum. The web was dried using two through air drier drums to 90% solids before being transferred to a steam heated Yankee dryer cylinder. The Yankee dryer had 18 mg/m$^2$ of a PAE based adhesive applied as well as 45 mg/m$^2$ of a polyvinyl alcohol and 3 mg/m$^2$ of a release oil applied using a double overlap spraybar. The sheet was creped from the Yankee dryer using a 45 degree ceramic blade at 98% solids and reeled into parent rolls.

Two wipe parent roll webs were laminated together using embossing using the deco configuration (only the top sheet is embossed with glue applied to the inside of the top sheet at the high points derived from the embossments using an adhesive supplied by an applicator roll) with the second exterior layer of each web facing each other. The top sheet emboss roll used a pattern with 20% contact with the applicator roll. The binder used was a copolymer of vinyl acetate-ethylene dispersion purchased from Wacker of Munchen, Germany under the product name of VINNAPAS® 400 and 20% polyvinyl alcohol purchased from Sekisui under the tradename Selvol™ 523. The binder was diluted to 25% solids. The laminated wipes were then cut to size and packaged in a wetting solution to a solids concentration of 30%. The wetting solution was 95% purified water, 4.4% boric acid with the remainder a mixture of humectants, preservatives, moisturizers, surfactants, chelating agents, pH buffer, and aromatic compounds Example 3

A flat pack of 2-ply pre-moistened wipes (30% solids) with dimensions of 5.25 inches by 7 inches were manufactured using the wet-laid TAD process and laminated using the deco emboss method with an 80% vinyl acetate-ethylene copolymer, 20% polyvinyl alcohol binder. The resulting 2-ply product had the following product attributes: Basis Weight 75 g/m², MD tensile of 62 N/m, CD tensile of 54.2 N/m, caliper of 1.050 mm and a burst strength of 2183 gf.

The wipe web was formed on a wet laid TAD asset with a twin wire solid C-wrap former with a 3 layer headbox. The furnish to each layer was composed of 80% Grand Prairie NB SK and 20% 4 mm Lyocell fiber co-refined imparting 120 kwh/ton. 2 kg/ton of glyoxalated polyacrylamide (Hercobond™ 1194 from Solenis of Wilmington Del.) was added to the co-refined NBSK and Lyocell at the discharge of the refiner. 2 kg/ton of carboxymethyl cellulose from Ashland (50 East River Center Boulevard Covington Ky. 41011) was added at the discharge of the refiner. 10 kg/ton of Redibond® 2038 amphoteric starch from Ingredion (5 Westbrook Corporate Center Westchester, Ill. 60154) and 2 kg/ton of Hercobond 6350 polyvinyl amine from Solenis was added to the suction of each of the three layer fan pumps. The fiber and chemicals mixtures were diluted to a solids of 0.5% consistency and fed to separate fan pumps which delivered the slurry to the triple layered headbox. The headbox pH was controlled to 7.0 by addition of a caustic to the thick stock before the fan pumps. The headbox deposited the slurry to a nip formed by a forming roll, an outer forming wire, and an inner fabric. The slurry was drained through the outer wire, which was a KT194-P design from Asten Johnson, and transferred to a plain weave inner wire. The web was then transferred to a structured TAD fabric with a 10 shed weave, 0.35 mm warp and 0.50 mm shute monofilament, at 15% wire crepe. A single slotted vacuum box of 18 mm with 35 kPa of vacuum was used to facilitate transfer to the structured fabric upon which the web traveled over a four slotted molding box (each slot at 19 mm), with 80 kPa of vacuum. The web was dried using two through air drier drums to 90% solids before being transferred to a steam heated Yankee dryer cylinder. The Yankee dryer had 18 mg/m² of a PAE based adhesive applied as well as 45 mg/m² of a polyvinyl alcohol and 3 mg/m² of a release oil applied using a double overlap spraybar. The sheet was creped from the Yankee dryer using a 45 degree ceramic blade at 98% solids and reeled into parent rolls.

Two wipe parent roll webs were laminated together using embossing using the deco configuration (only the top sheet is embossed with glue applied to the inside of the top sheet at the high points derived from the embossments using an adhesive supplied by an applicator roll) with the second exterior layer of each web facing each other. The top sheet emboss roll used a pattern with 13% coverage with round elements 0.115 inches diameter and 0.135 inches in depth. The binder used was a copolymer of vinyl acetate-ethylene dispersion purchased from Wacker of Munchen, Germany under the product name of VINNAPAS® 400 and 20% polyvinyl alcohol purchased from Sekisui under the tradename Selvol 523. The laminated wipes were then cut to size and packaged in a wetting solution to a solids concentration of 30%. The wetting solution was 95% purified water, 4.4% boric acid with the remainder a mixture of humectants, preservatives, moisturizers, surfactants, chelating agents, pH buffer, and aromatic compounds.

Example 4

Multiple flat packs of 2-ply pre-moistened wipes (30% solids) with dimensions of 5.25 inches by 7 inches were manufactured using the wet-laid TAD process and laminated using the deco emboss method with an 80% vinyl acetate-ethylene copolymer, 20% polyvinyl alcohol binder.

The wipe web was formed on a wet laid TAD asset with a twin wire solid C-wrap former with a 3 layer headbox. The furnish to all layers was 80% Grand Prairie NBSK and 20% 6 mm Lyocell. This NBSK and Lyocell were co-refined in a conical refiner imparting 140 kwhr/ton. 4 kg/ton of glyoxalated polyacrylamide (Hercobond™ 1194 from Solenis of Wilmington, Del.) was added to the corefined NBSK and Lyocell at the discharge of the refiner. 3 kg/ton of OmyaSoft™ 140 ground calcium carbonate from Omya Inc (9987 Carver Road Suite 300 Cincinnati Ohio 45242) was added to the suction of the refiner. 10 kg/ton of Redibond® 2038 amphoteric starch from Ingredion (5 Westbrook Corporate Center Westchester, Ill. 60154) and 2 kg/ton of Hercobond™ 6350 polyvinyl amine from Solenis was added to the suction of each of the three layer fan pumps. The fiber and chemicals mixtures were diluted to a solids of 0.5% consistency and fed to separate fan pumps which delivered the slurry to the triple layered headbox. The headbox pH was controlled to 7.0 by addition of a caustic to the thick stock before the fan pumps. The headbox deposited the slurry to a nip formed by a forming roll, an outer forming wire, and an inner fabric. The slurry was drained through the outer wire, which was a KT194-P design from Asten Johnson of Charleston, S.C., and transferred to a plain weave inner wire. The web was then transferred to a structured TAD fabric with a 10 shed weave, 0.35 mm warp and 0.50 mm shute monofilament, at 15% wire crepe. A single slotted vacuum box of 18 mm with 35 kPa of vacuum was used to facilitate transfer to the structured fabric upon which the web traveled over a four slotted molding box (each slot at 19 mm), with 80 kPa of vacuum. The web was dried using two through air drier drums to 90% solids before being transferred to a steam heated Yankee dryer cylinder. The Yankee dryer had 18 mg/m² of a PAE based adhesive applied as well as 45 mg/m² of a polyvinyl alcohol and 3 mg/m² of a release oil applied using a double overlap spraybar. The sheet was creped from the Yankee dryer using a 45 degree ceramic blade at 98% solids and reeled into parent rolls.

Two wipe parent roll webs were laminated together using embossing using the deco configuration (only the top sheet is embossed with glue applied to the inside of the top sheet at the high points derived from the embossments using an adhesive supplied by an applicator roll) with the second exterior layer of each web facing each other. The top sheet emboss roll used a pattern with 20% contact with the applicator roll. The binder used was a copolymer of vinyl acetate-ethylene dispersion purchased from Wacker of Munchen, Germany under the product name of VINNAPAS® 400 and 20% polyvinyl alcohol purchased from Sekisui under the tradename Selvol 523. The binder was diluted to 25% solids. The laminated wipes were then cut to size and packaged in a wetting solution to a solids concentration of 30%. The wetting solutions had different concentrations of boric acid and sodium bicarbonate added resulting in different wipe tensile strengths as shown in Table 1. Without being bound by theory, it is believed sodium borate was produced when adding both the boric acid and sodium bicarbonate. This salt prevented the binder (vinyl acetate-ethylene and polyvinyl alcohol) and additives (glyoxalated polyacrylamide, starch, calcium carbonate, and polyvinyl amine) from solubilizing and allowed these chemicals to remain bound to the fibers and impart strength even while in the wetting solution.

TABLE 1

| Test Name | % Boric Acid | % Sodium Bicarbonate | pH | MD Tensile N/m | CD Tensile N/m |
|---|---|---|---|---|---|
| Cell 1 | 1% | 0% | 4.93 | 87 | 71 |
| Cell 2 | 2% | 0% | 4.88 | 91 | 79 |
| Cell 3 | 3% | 0% | 4.44 | 91 | 83 |
| Cell 4 | 4% | 0% | 4.15 | 96 | 84 |
| Cell 5 | 4% | 8% | 7.5 | 143 | 119 |
| Cell 6 | 4% | 4% | 7.22 | 140 | 117 |
| Cell 7 | 4% | 2% | 6.94 | 130 | 110 |
| Cell 8 | 4% | 1% | 6.67 | 105 | 91 |

Example 5

A flat pack of 2-ply pre-moistened wipes (30% solids) with dimensions of 5.25 inches by 7 inches were manufactured using the wet-laid TAD process and laminated using the deco emboss method with an 80% vinyl acetate-ethylene copolymer, 20% polyvinyl alcohol binder. The resulting 2-ply product had the following product attributes: Basis Weight 61 g/m$^2$, Caliper 0.961 mm, MD tensile of 240 N/m, CD tensile of 200 N/m.

The wipe web was formed on a wet laid TAD asset with a twin wire solid C-wrap former with a 3 layer headbox. The furnish to all layers was 100% Grand Prairie NBSK. This NBSK was refined in a conical refiner imparting 90 kwhr/ton. 3 kg/ton of glyoxalated polyacrylamide (Luredur® Pluss 555 from BASF Corporation 100 Park Ave., Florham Park, N.J. 07932+1 800 526–1072) was added to the refined NBSK at the discharge of the refiner. The fiber and chemicals mixtures were diluted to a solids of 0.5% consistency and fed to separate fan pumps which delivered the slurry to the triple layered headbox. The headbox pH was controlled to 7.0 by addition of a caustic to the thick stock before the fan pumps. The headbox deposited the slurry to a nip formed by a forming roll, an outer forming wire, and an inner fabric. The slurry was drained through the outer wire, which was a KT194-P design from Asten Johnson of Charleston, S.C., and transferred to a plain weave inner wire. The web was then transferred to a structured TAD fabric with a 10 shed weave, 0.35 mm warp and 0.50 mm shute monofilament, at 15% wire crepe. A single slotted vacuum box of 18 mm with 35 kPa of vacuum was used to facilitate transfer to the structured fabric upon which the web traveled over a molding box (each slot at 19 mm), with 80 kPa of vacuum. The web was dried using two through air drier drums to 90% solids before being transferred to a steam heated Yankee dryer cylinder. The Yankee dryer had 18 mg/m$^2$ of a PAE based adhesive applied as well as 45 mg/m$^2$ of a polyvinyl alcohol and 3 mg/m$^2$ of a release oil applied using a double overlap spraybar. The sheet was creped from the Yankee dryer using a 45 degree ceramic blade at 98% solids and reeled into parent rolls.

Two wipe parent roll webs were laminated together using embossing using the deco configuration (only the top sheet is embossed with glue applied to the inside of the top sheet at the high points derived from the embossments using an adhesive supplied by an applicator roll) with the second exterior layer of each web facing each other. The top sheet emboss roll used a pattern with 20% contact with the applicator roll. The binder used was a copolymer of vinyl acetate-ethylene dispersion purchased from Wacker of Munchen, Germany under the product name of VINNAPAS® 400 and 20% polyvinyl alcohol purchased from Sekisui under the tradename Selvol 523. The binder was diluted to 25% solids. The laminated wipes were then cut to size and packaged in a wetting solution to a solids concentration of 30%. The wetting solution had 4% boric acid and 2% sodium bicarbonate. Without being bound by theory, it is believed sodium borate was produced when adding both the boric acid and sodium bicarbonate. This salt prevented the binder (vinyl acetate-ethylene and polyvinyl alcohol) and additives (glyoxalated polyacrylamide) from solubilizing and allowed these chemicals to remain bound to the fibers and impart strength even while in the wetting solution.

All of the wipes described in Examples 1 to 5 above passed the slosh box disintegration test described in INDA FG502.

Table 2 shows comparative test results for the products made in accordance with Examples 1, 2 and 3 and for commercially available products. For Examples 1, 2 and 3, the test results are shown for basis weight (i.e., before the addition of a wetting solution), machine direction tensile strength, and burst strength of the wipe product after addition of the wetting solution or deionized water. The wetting solution or deionized water was added to obtain a 30% solids concentration.

TABLE 2

| Product | BW(2-Ply) Bone Dry g/m$^2$ | MD Tensile N/m | Burst (75% by wt. DI water) gf | Tensile (75% by wt. 4.4% boric acid) gf | Location | Date |
|---|---|---|---|---|---|---|
| Example 3 (75% by wt. DI water) | 75 | 49 | 1590 | 2183 | n/a | n/a |
| Example 3 (75% by wt. 4.4% boric acid) | 75 | 62 | 1590 | 2183 | n/a | n/a |
| Example 2 (75% by wt. DI water) | 74 | 69 | 1845 | 2404 | n/a | n/a |
| Example 2 (75% by wt. 4.4% boric acid) | 74 | 76 | 1845 | 2404 | n/a | n/a |

TABLE 2-continued

| Product | BW(2-Ply) Bone Dry g/m² | MD Tensile N/m | Burst (75% by wt. DI water) gf | Tensile (75% by wt. 4.4% boric acid) gf | Location | Date |
|---|---|---|---|---|---|---|
| Example 1 (75% by wt. DI water) | 82 | 46 | 1522 | 1848 | n/a | n/a |
| Example 1 (75% by wt. 4.4% boric acid) | 82 | 56 | 1522 | 1848 | n/a | n/a |
| Cottonelle Fresh Care | 80 | 80 | 4703 | | Sam's Club Greenville, SC | June 2015 |
| Kirkland Signature | 69 | 268 | 7701 | | Costco Greenville, SC | June 2015 |

The tests confirm that the present invention is advantageous in that the addition of boric acid to the wetting solution improves the wet tensile and burst strength. The inventive wipes have comparable basis weight to the commercially available products and sufficient tensile and burst strength to provide functionality, but are flushable and dispersible.

Table 3 below provides data on the longest fiber measured using a microscope for each of Example 5 and commercially available products.

TABLE 3

| Product | Longest Fiber Length | Location | Date |
|---|---|---|---|
| Kirkland | 11.5 mm | Costo-Greenvile, SC | July 2016 |
| Cottonelle | 4.2 mm | Costo-Greenvile, SC | July 2016 |
| Charmin | 7.2 mm | Walmart-Anderson, SC | July 2016 |
| Scott | 4.7 mm | Walmart-Anderson, SC | July 2016 |
| Great Value | 7.9 mm | Walmart-Anderson, SC | July 2016 |
| Example 5 | 3.5 mm | | |

Table 4 below provides length weighted mean fiber length data for each of Example 5 and commercially available products.

TABLE 4

| Product | LWW (mm) | Location | Date |
|---|---|---|---|
| Scott Natural | 2.872 | Walmart-Anderson, SC | July 2016 |
| Cottonelle | 2.859 | Walmart-Anderson, SC | July 2016 |
| Example 5 | 3.022 | | |

Solvent extractions were performed on commercially available wipes and the wipe made in accordance with Example 5 to determine the amount of solvent-soluble, non-volatile material in the wipes. The solvent extractives test was performed in accordance with TAPPI T204 cm-07. The results are shown in Table 5.

TABLE 5

| Product | Mass of Dried Sample (g) | Mass of Extract (g) | % Extract |
|---|---|---|---|
| Scott | 1.8416 | 0.1916 | 10.40% |
| Cottonelle | 2.0087 | 0.2118 | 10.54% |
| Example 5 | 1.5162 | 0.0184 | 1.21% |
| Charmin | 1.5397 | 0.0288 | 1.87% |
| Kirkland | 1.7134 | 0.0185 | 1.08% |
| Great Value | 1.5819 | 0.0208 | 1.31% |

The Scott® and Cottonelle® wipes produced significantly more extract as compared to the other tested wipes. Fourier transform infrared spectroscopy (FTIR) was used to determine the chemical characteristics of the extract. The FTIR spectra for Scott® and Cottonelle® extracts showed significant similarities to polymers containing vinyl groups.

While particular embodiments of the invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A multi-ply flushable wet wipe that is devoid of fibers greater than 5 mm in length and that comprises less than 3% extractives as measured in accordance with the TAPPI T204 cm-07 test standard, the wet wipe being dispersible in accordance with the INDA FG502 test standard, wherein the wet wipe comprises a first ply and a second ply, each of the first and second plies have two external layers, and the first and second plies are laminated to one another by application of a binder to only one of the two external layers of the first ply or the second ply, wherein the only one of the two external layers of the first ply or the second ply is a layer that directly faces the other of the first ply or the second ply.

* * * * *